(12) United States Patent
Blaschuk et al.

(10) Patent No.: US 6,593,297 B2
(45) Date of Patent: *Jul. 15, 2003

(54) COMPOUNDS AND METHODS FOR INHIBITING CANCER METASTASIS

(75) Inventors: Orest W. Blaschuk, Westmount (CA); James Matthew Symonds, Ottawa (CA); Stephen Byers, Washington, DC (US); Barbara J. Gour, Kemptville (CA)

(73) Assignee: Adherex Technologies, Inc., Ottawa (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/264,516

(22) Filed: Mar. 8, 1999

(65) Prior Publication Data

US 2002/0169106 A1 Nov. 14, 2002

Related U.S. Application Data

(63) Continuation-in-part of application No. 09/234,395, filed on Jan. 20, 1999, which is a continuation-in-part of application No. 09/187,859, filed on Nov. 6, 1998, now Pat. No. 6,358,920, which is a continuation-in-part of application No. 09/073,040, filed on May 5, 1998, now Pat. No. 6,472,367.

(51) Int. Cl.[7] ..................... A61K 31/395; A61K 38/08; A61K 38/12; A61K 38/18
(52) U.S. Cl. ............................... 514/12; 514/9; 514/11; 514/13; 514/14; 514/15; 514/16; 514/17; 424/130.1
(58) Field of Search .................. 514/9, 11, 12, 514/13–17; 424/130.1

(56) References Cited

U.S. PATENT DOCUMENTS

| 5,597,725 A | 1/1997 | Suzuki |
| 5,639,634 A | 6/1997 | Suzuki |
| 5,646,250 A | 7/1997 | Suzuki |
| 5,811,514 A | 9/1998 | Bard et al. |
| 5,916,771 A | 6/1999 | Hori et al. |
| 6,031,072 A | 2/2000 | Blaschuk et al. ........... 530/317 |

FOREIGN PATENT DOCUMENTS

| GB | 2 282 379 A | 4/1995 |
| WO | WO 91/04745 | 4/1991 |
| WO | WO 96/27387 | 9/1996 |
| WO | WO 98/02452 | 1/1998 |
| WO | WO 00/02917 | 1/2000 |

OTHER PUBLICATIONS

Ther Merck Manual Diagnosis and Therapy (16th edition) 1992 p. 1265.*
Taber's Cyclopedic Medical Dictionary (17th edition) 1993 p. 1016.*
Tomita et al. Cancer Research, 60:3650–3654, Jul. 2000.*
Feltes et al. Cancer Research, 62:6688–6697, Nov. 2002.*
Kimura et al. "Cadherin–11 expressed in association with mesenchymal morphogenesis in the head, somite, and limb bud early mouse embryos," *Dev Biol.* 169(1):347–358, May 1995.
Kools et al., "Expression in mesenchymal tumors of alternative cadherin–11 transcripts encoding truncated adhesion molecules: a mechanism for acquiring invasive properties?," *Clinical & Experimental Metastasis* 14(Suppl. 1):52–53, Sep. 1996.
Pishvaian et al., "Cadherin–11 is expressed in invasive breast cancer cell lines," *Cancer Res.* 59(40:947–952, Feb. 15, 1999.
Yin et al., "TGF–b signaling blockade inhibits PTHrP secretion by breast cancer cells and bone metastases development," *J Clin Invest.* 103(2):197–206, Jan. 1999.
Yoneda et al., "Inhibition of osteolytic bone metastasis of breast cancer combined treatment with the bisphosphonate ibandronate and tissue inhibitor of the matrix metalloproteinase–2," *J Clin Invest.* 99(10):2509–2517, May 15, 1997.
Munro, S. et al., Experimental and Molecular Pathology, 62(2):118–122, 1995 Abstract Only.
Bussemakers et al., "The role of OB–cadherin in human prostate cancer," in *Proceedings of the American Association for Cancer Research*, vol. 39, New Orleans, LA, Mar., 1998, p. 500.
Albelda et al., "Adhesion Molecules and Inflammatory Injury," *FASEB J.* 8(8): 504–512, 1994.
Edgington, "How Sweet It Is: Selectin–Mediating Drugs," *Bio/Technology* 10(4): 383–389, 1992.
Kahan, "Immunosuppressive Therapy," *Current Opinion in Immunology* 4(5): 553–560, 1992.
Lutz et al., "Antibody Recognition of Peptide Sequences from the Cell–Cell Adhesion Proteins: N– and E–cadherins," *Peptide Research* 9(5): 233–239, 1996.
Slootstra et al., "Structural Aspects of Antibody–Antigen Interaction Revealed Through Small Random Peptide Libraries," *Molecular Diversity* 1: 87–96, 1995.

(List continued on next page.)

Primary Examiner—Marianne P. Allen
(74) Attorney, Agent, or Firm—Seed Intellectual Property Law Group PLLC

(57) ABSTRACT

Agents for inhibiting cancer metastasis are provided. The methods comprise administering to a patient an antimetastatic agent that comprises one or more of: (a) a peptide sequence that is at least 50% identical to an OB-cadherin CAR sequence; (b) a non-peptide mimetic of an OB-cadherin CAR sequence; (c) a substance, such as an antibody or antigen-binding fragment thereof, that specifically binds an OB-cadherin CAR sequence; and/or (d) a polynucleotide encoding a polypeptide that comprises an OB-cadherin CAR sequence or analogue thereof.

14 Claims, 6 Drawing Sheets

OTHER PUBLICATIONS

Tanihara et al., "Cloning of Five Human Cadherins Clarifies Characteristic Features of Cadherin Extracellular Domain and Provides Further Evidence for Two Structurally Different Types of Cadherin," *Cell Adhesion and Communications 2*: 15–26, 1994.

Ward and Mulligan, "Blocking of Adhesion Molecules In Vivo as Anti–Inflammatory Therapy," *Therapeutic Immunology 1*: 165–171, 1994.

Getsios et al., "Regulated Expression of Cadherin–6 and Cadherin–11 in the Glandular Epithelial and Stromal Cells of the Human Endometrium," *Developmental Dynamics 211*: 238–247, 1998.

Matsuyoshi and Imamura, "Multiple Cadherins Are Expressed in Human Fibroblasts," *Biochemical And Biophysical Research Communications 235*: 355–358, 1997.

Munro and Blashchuk, In: *Cell Adhesion and Invasion in Cancer Metastasis*, P. Brodt (ed.), RG Landes Co., Austin, Texas, 1996, Chapter 3, "The Structure, Function and Regulation of Cadherins," pp. 17–34.

Okazaki et al., "Molecular Cloning and Characterization of OB–cadherin, a New Member of Cadherin Family Expressed in Osteoblasts," *The Journal of Biological Chemistry 269*(16): 12092–12098, 1994.

Shibata et al., "Simultaneous expression of cadherin–11 in signet–ring cell carcinoma and stromal cells of diffuse–type gastric cancer," *Cancer Letters 99*: 147–153, 1996.

Shimazui et al., "Complex Cadherin Expression in Renal Cell Carcinoma," *Cancer Research 56*: 3234, 3237, 1996.

Simonneau et al., "Cadherin 11 Expression Marks the Mesenchymal Phenotype: Towards New Functions for Cadherins?," *Cell Adhesion and Communication 3*: 115–130, 1995.

Suzuki et al., "Diversity of the cadherin family: evidence for eight new cadherins in nervous tissue," *Cell Regulation 2*: 261–270, 1991.

* cited by examiner

```
Human   G W V W N Q F F V I E E Y T G P D P V L V G R L H S D I D S G D G N I K Y I L S G E G A G
Mouse   G W V W N Q F F V I E E Y T G P D P V L V G R L H S D I D S G D G N I K Y I L S G E G A G
Chicken G W V W N Q F F V I E E Y T G P D P V L V G R L H S D I D S G D G N I K Y I L S G E G A G Human   T I F V I D D K S G N I H A T K T L D R E E R A Q Y T L M A Q A V D R D T N R P L E P P S
Mouse   T I F V I D D K S G N I H A T K T L D R E E R A Q Y T L M A Q A V D R D T N R P L E P P S
Chicken I I F V I D D K S G N I H A T K T L D R E E R A Q Y T L T A Q A V D R N T N R P L E P P S Human   E F I V K V Q D I N D N P P E F
Mouse   E F I V K V Q D I N D N P P E F
Chicken E F I V K V Q D I N D N P P E F
```

*Fig. 1*

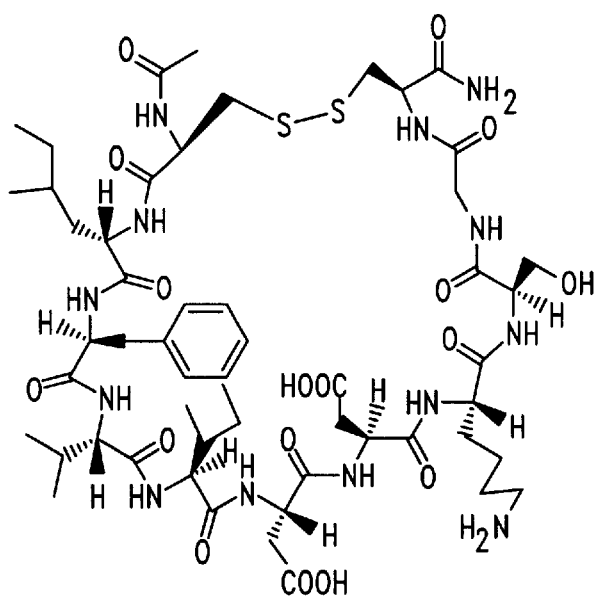
N-Ac-<u>CIFVIDDKSGC</u>-NH$_2$
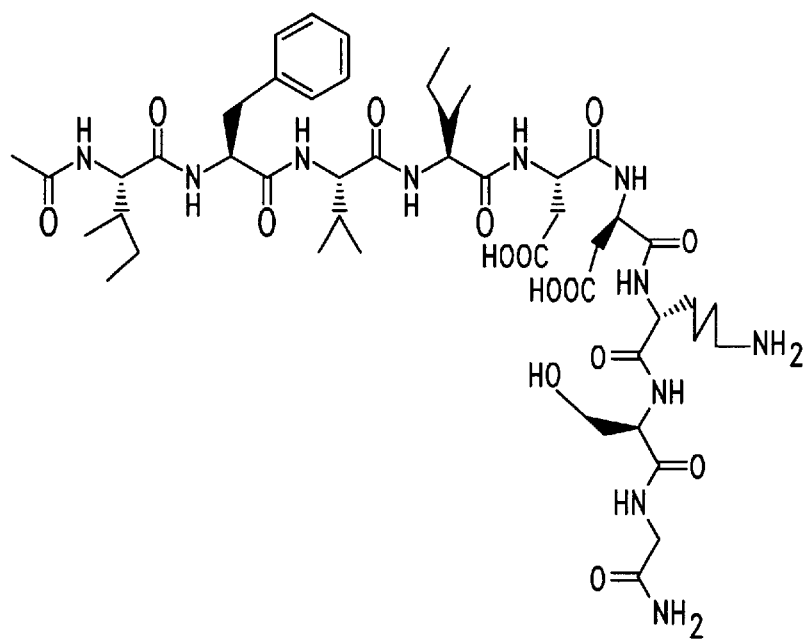
N-Ac-IFVIDDKSG-NH$_2$
*Fig. 2A*

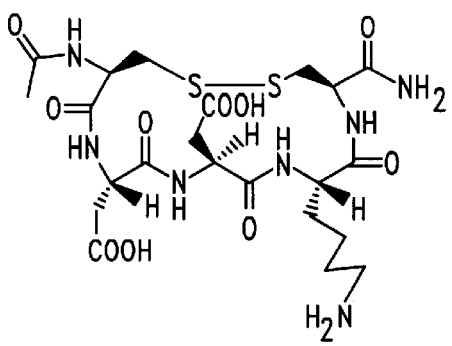
N-Ac-CDDKC-NH₂
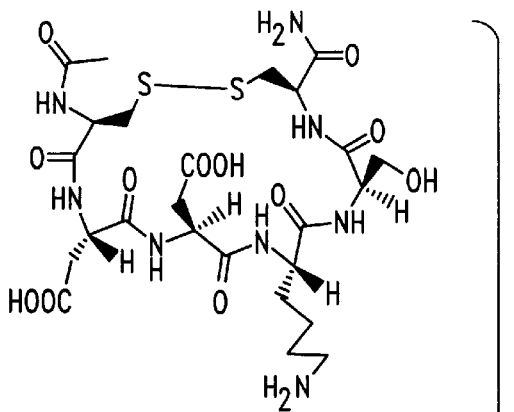
N-Ac-CDDKSC-NH₂
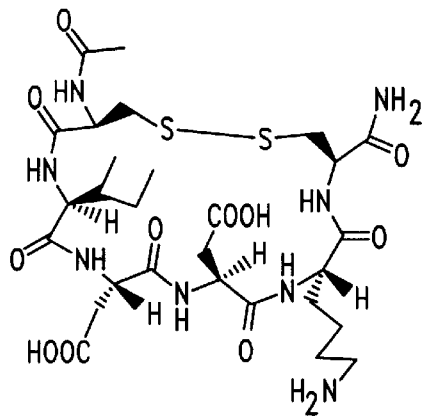
N-Ac-CIDDKC-NH₂
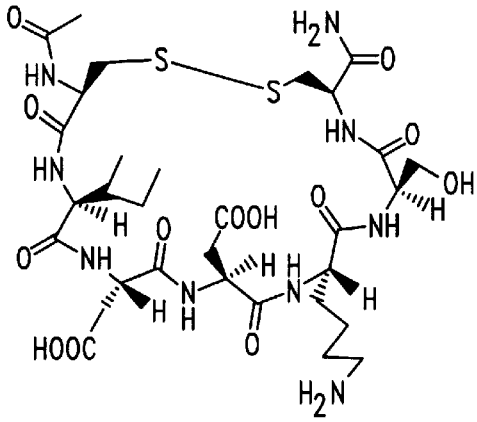
N-Ac-CIDDKSC-NH₂
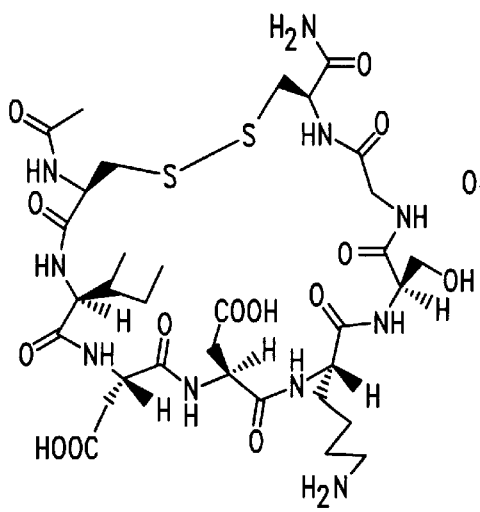
N-Ac-CIDDKSGC-NH₂
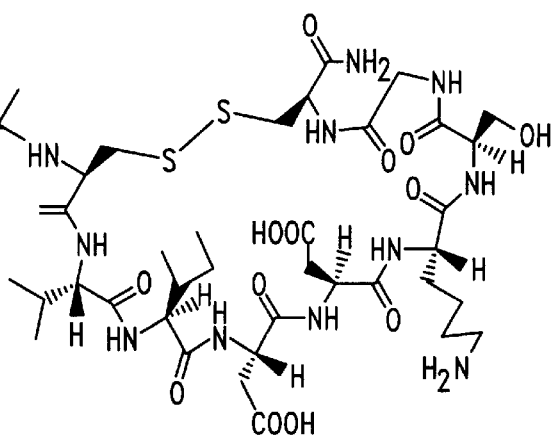
N-Ac-CVIDDKSGC-NH₂
*Fig. 2B*

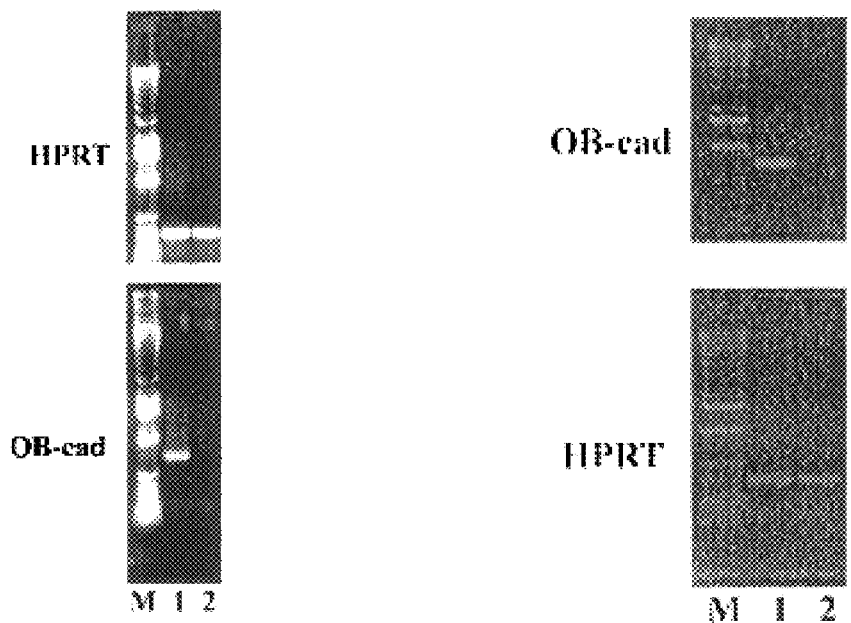
*Fig. 4*
*Fig. 5*
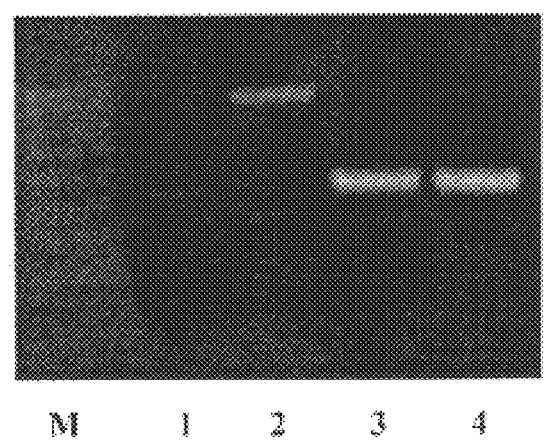
*Fig. 6*

COMPOUNDS AND METHODS FOR INHIBITING CANCER METASTASIS

CROSS-REFERENCE TO RELATED APPLICATIONS

This application is a continuation-in-part of U.S. Ser. No. 09/234,395, filed Jan. 20, 1999; which is a continuation-in-part of U.S. Ser. No. 09/187,859, filed Nov. 6, 1998 now U.S. Pat. No. 6,358,920; which is a continuation-in-part of U.S. Ser. No. 09/073,040, filed May 5, 1998 now U.S. Pat. No. 6,472,367.

TECHNICAL FIELD

The present invention relates generally to methods for inhibiting cancer metastasis, and more particularly to the use of OB-cadherin peptides, and antibodies that bind such peptides, to inhibit adhesion and metastasis of circulating cancer cells.

BACKGROUND OF THE INVENTION

Cancer is a significant health problem throughout the world. Although advances have been made in detection and therapy of cancer, no vaccine or other universally successful method for prevention or treatment is currently available. One reason for failure of a cancer treatment is often the growth of secondary metastatic lesions in distant organs. Therapy for metastasis currently relies on a combination of early diagnosis and aggressive treatment, which may include radiotherapy, chemotherapy or hormone therapy. However, the toxicity of such treatments limits the use of presently available anticancer agents for treatment of malignant disease. The high mortality rate for many cancers indicates that improvements are needed in metastasis prevention and treatment.

The development of less toxic antimetastatic agents would facilitate the long term treatment of latent or residual disease. Such agents could also be used prophylactically after the removal of a precancerous tumor. It has been suggested that certain agents that inhibit metastasis may function by inhibiting adhesion of cancer cells. For example, WO 97/00956 describes the use of an antibody raised against an adhesion protein on endothelial and muscle cells for inhibiting tumor metastasis.

Accordingly, there is a need in the art for the development of further methods for inhibiting cancer metastasis. The present invention fulfills these needs and further provides other related advantages.

SUMMARY OF THE INVENTION

Briefly stated, this invention provides compositions and methods for inhibiting cancer metastasis. Within certain aspects, antimetastatic agents are provided. Such agents may: (a) comprise a peptide sequence that is at least 50% identical to an OB-cadherin CAR sequence; and (b) inhibit OB-cadherin mediated cell adhesion. Certain antimetastatic agents comprise an OB-cadherin CAR sequence and are peptides ranging in size from 3 to 50, preferably from 4 to 16, amino acid residues.

Within certain embodiments, an antimetastatic agent comprises an OB-cadherin CAR sequence that is present within a cyclic peptide. Such cyclic peptides may have the formula:

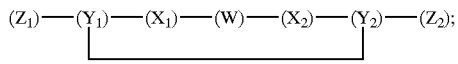

wherein W is a tripeptide selected from the group consisting of EEY, DDK and EAQ; wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds.

Within certain specific embodiments, an antimetastatic agent as provided herein may comprise: (a) one or more OB-cadherin CAR sequences selected from the group consisting of DDK, IDDK (SEQ ID NO:37) DDKS (SEQ ID NO:38), VIDDK (SEQ ID NO:39), IDDKS (SEQ ID NO:40), VIDDKS (SEQ ID NO:41), DDKSG (SEQ ID NO:42), IDDKSG (SEQ ID NO:43), VIDDKSG (SEQ ID NO:44), FVIDDK (SEQ ID NO:45), FVIDDKS (SEQ ID NO:46), FVIDDKSG (SEQ ID NO:47), IFVIDDK (SEQ ID NO:48), IFVIDDKS (SEQ ID NO:49), IFVIDDKSG (SEQ ID NO:50), EEY, IEEY (SEQ ID NO:51), EEYT (SEQ ID NO:52), VIEEY (SEQ ID NO:53), IEEYT (SEQ ID NO:54), VIEEYT (SEQ ID NO:55), IEEYTG (SEQ ID NO:57), IEEYTG (SEQ ID NO:56), VIEEYTG (SEQ ID NO:58), FVIEEY (SEQ ID NO:59), FVIEEYT (SEQ ID NO:60), FVIEEYTG (SEQ ID NO:61), FFVIEEY (SEQ ID NO:62), FFVIEEYT (SEQ ID NO:63), FFVIEEYTG (SEQ ID NO:64), EAQ, VEAQ (SEQ ID NO:65), EAQT (SEQ ID NO:66), SVEAQ (SEQ ID NO:67), VEAQT (SEQ ID NO:68), SVEAQT (SEQ ID NO:69), EAQTG (SEQ ID NO:70), VEAQTG (SEQ ID NO:71), SVEAQTG (SEQ ID NO:72), FSVEAQ (SEQ ID NO:73), FSVEAQT (SEQ ID NO:74), FSVEAQTG (SEQ ID NO:75), YFSVEAQ (SEQ ID NO:76), YFSVEAQT (SEQ ID NO:77) and YFSVEAQTG (SEQ ID NO:78); or (b) an analogue of any of the foregoing sequences that differs in one or more substitutions, deletions, additions and/or insertions such that that ability of the analogue to modulate an OB-cadherin-mediated function is not substantially diminished. For example, the agent may comprise a linear peptide having the sequence N-Ac-IFVIDDKSG-NH$_2$ (SEQ ID NO:50), N-Ac-FFVIEEYTG-NH$_2$ (SEQ ID NO:64) or N-Ac-YFSVEAQTG-NH$_2$ (SEQ ID NO:78). The OB-cadherin CAR sequence may, but need not, be present within a cyclic peptide.

The present invention further provides antimetastatic agents that comprise an antibody or antigen-binding fragment thereof that specifically binds to an OB-cadherin CAR sequence and modulates OB-cadherin-mediated cell adhesion.

Within further aspects, the present invention provides antimetastatic agents comprising a non-peptide mimetic of an OB-cadherin CAR sequence.

Any of the above antimetastatic agents may, within certain embodiments, be linked to one or more of a drug, detectable marker, targeting agent or support material. Alternatively, or in addition, an antimetastatic agent as described above, may further comprise one or more of: (a) a CAR sequence that is specifically recognized by an adhesion molecule other than OB-cadherin; and/or (b) an antibody or antigen-binding fragment thereof that specifically binds to a CAR sequence that is specifically recognized by an adhesion molecule other than OB-cadherin. For example, such an adhesion molecule may be cadherin-5, cadherin-6, occludin, claudin, N-CAM, PE-CAM, CEA, L1, JAM, an integrin or N-cadherin.

Within other aspects, the present invention provides pharmaceutical compositions comprising an antimetastatic agent as described above in combination with a physiologically acceptable carrier. Within such compositions, the antimetastatic agent may, but need not, be present within a sustained-release formulation. Such compositions may, within certain embodiments, further comprise a drug and/or a modulator of cell adhesion that comprises one or more of: (a) a CAR sequence that is specifically recognized by an adhesion molecule other than OB-cadherin; and/or (b) an antibody or antigen-binding fragment thereof that specifically binds to a CAR sequence that is specifically recognized by an adhesion molecule other than OB-cadherin.

The present invention further provides, within other aspects, methods for inhibiting cancer metastasis. Such methods generally comprise administering to a patient an antimetastatic agent as described above, or a polynucleotide encoding such an agent. The patient may be afflicted with a cancer such as a carcinoma, leukemia or melanoma, and the antimetastatic agent may be administered to the tumor or systemically. Within such methods, the antimetastatic agent may, but need not, be present within a pharmaceutical composition as recited above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 provides the amino acid sequences of representative mammalian GB-cadherin EC1 domains, human OB-cadherin (SEQ ID NO:1) and mouse OB-cadherin (SEQ ID NO:2) and chicken OB-cadherin (SEQ ID NO:3).

FIGS. 2A–2C provide structures of representative antimetastatic agents (SEQ ID NOS: 50, 79–84, 86, 87, 93, 107, 114, 127).

FIG. 3A shows the cells 24 hours after exposure to 100 µl water/1 ml culture medium (magnification 200×). FIGS. 3B and 3C show the cells 24 hours after exposure to 100 µL of a solution containing 10 mg/mL N-Ac-IFVIDDKSG-NH$_2$ (SEQ ID NO:50) per 1 mL culture medium (magnifications of 200× and 100×, respectively). Arrows indicate rounded cells.

FIG. 4 is a photograph illustrating the results of PCR analysis to detect the presence of OB-cadherin in metastatic human ovarian cancer cells, but not in well-differentiated human ovarian cancer cells. RT-PCR products from two cell lines are shown: SKOV3 in lane 1 and OVCAR3 in lane 2. The primers used were specific for OB-cadherin (OB-cad) and hypoxanthine phosphoribosyltransferase (HPRT) as indicated, with an expected PCR product of 745 bp and 352 bp, respectively. Products were stained with ethidium bromide and resolved by agarose gel electrophoresis. Lane M represents a 1 kb ladder (Gibco/BRL).

FIG. 5 is a photograph illustrating the results of PCR analysis detecting the presence of OB-cadherin in leukemic cells. RT-PCR products were generated from lymphocytes of a human B-CLL patient (lane 1) and mouse liver (lane 2). The primers used were specific for OB-cadherin (OB-cad, top panel) and hypoxanthine phosphoribosyltransferase (HPRT, bottom panel), with an expected PCR product of 745 bp and 352 bp, respectively. Products were stained with ethidium bromide and resolved by agarose gel electrophoresis. Lane M represents a 1 kb ladder (Gibco/BRL).

FIG. 6 is a photograph illustrating the results of PCR analysis detecting the presence of OB-cadherin in leukemic cells. RT-PCR products were generated from lymphocytes of a normal human (lanes 1 and 3) and a human B-CLL patient (lanes 2 and 4). The primers used were specific for OB-cadherin (lanes 1 and 2) and hypoxanthine phosphoribosyltransferase (HPRT; lanes 3 and 4), with an expected PCR product of 745 bp and 352 bp, respectively. Products were stained with ethidium bromide and resolved by agarose gel electrophoresis. Lane M represents a 1 kb ladder (Gibco/BRL).

DETAILED DESCRIPTION OF THE INVENTION

Figure 2C:
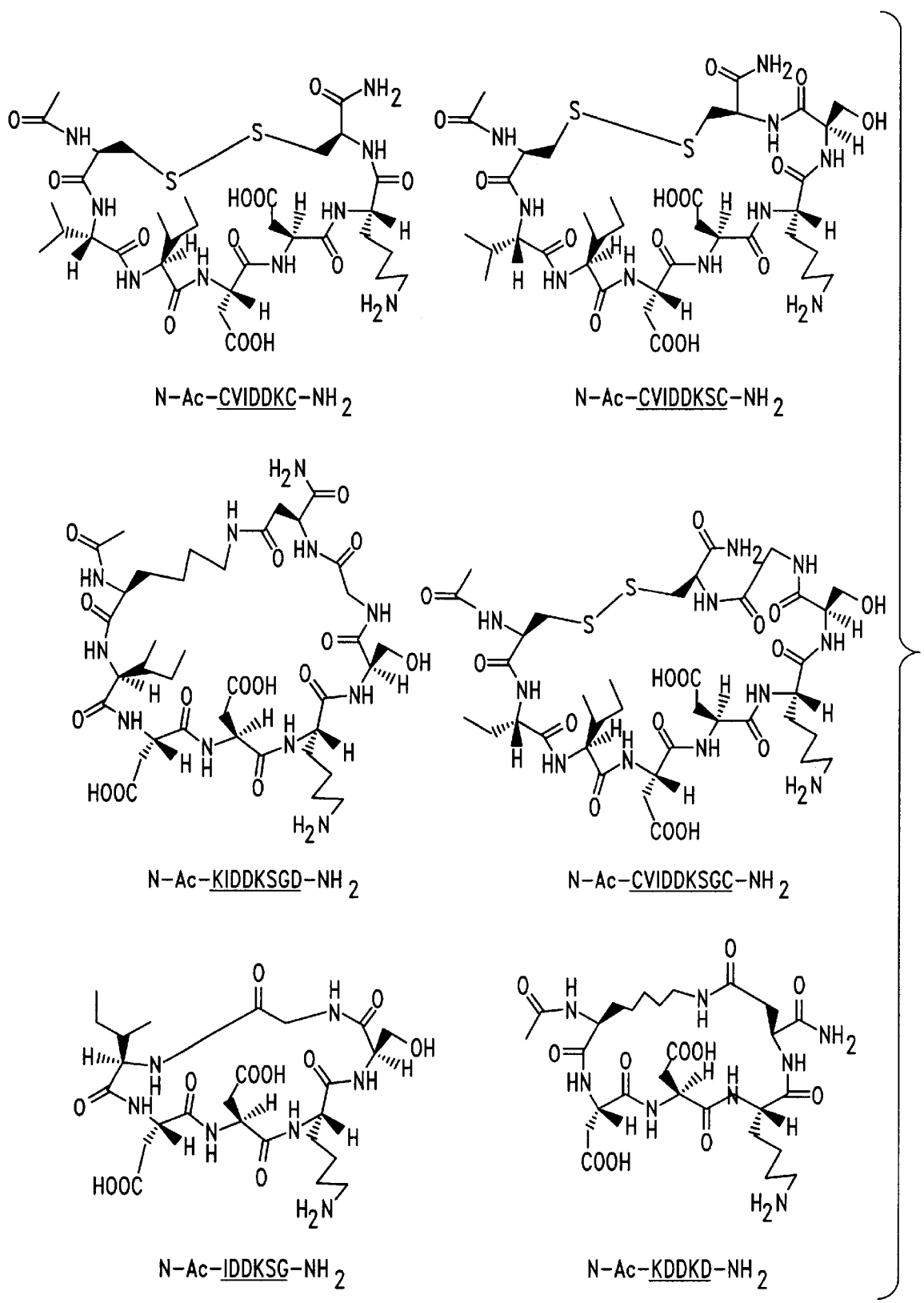

As noted above, the present invention provides methods for inhibiting cancer metastasis. The methods provided herein are based, in part, on the identification of OB-cadherin cell adhesion recognition (CAR) sequences, and on the discovery that OB-cadherin is expressed by certain metastatic carcinoma cells, but not by highly differentiated, poorly invasive carcinomas. Cancer metastasis may be inhibited (i.e., prevented, diminished in severity or delayed) by the administration of agents that inhibit OB-cadherin mediated cell adhesion. Such antimetastatic agents may be peptides that correspond to an OB-cadherin CAR sequence, or may be binding agents, such as antibodies and fragments thereof, that specifically recognize an OB-cadherin CAR sequence. In general, within the methods provided herein, an antimetastatic agent is administered to a patient in an amount sufficient to inhibit metastasis.

OB-CADHERIN

As used herein, the term "OB-cadherin" refers to certain cell adhesion molecules that are expressed by a human or non-human individual, and that are substantially homologous to a known OB-cadherin (also known as cadherin-11; and as discussed, for example, in Munro et al., *In: Cell Adhesion and Invasion in Cancer Metastasis*, P. Brodt, ed., pp. 17–34, RG Landes Co., Austin Tex., 1996; Getsios et al., *Developmental Dynamics* 211:238–247, 1998; Simonneau et al., *Cell Adhesion and Communication* 3:115–130, 1995; Okazaki et al., *J. Biological Chemistry* 269:12092–12098, 1994). Certain OB-cadherin molecules comprise a sequence provided in FIG. 1, but the present invention also contemplates the use of OB-cadherin from other organisms, as well as OB-cadherin variants that may have additional amino acids or may be truncated, as described below. OB-cadherin sequences may generally be identified based upon similarity to the sequences provided herein and based upon the presence of OB-cadherin activity, using an assay provided herein.

An OB-cadherin also contains characteristic cadherin repeats, but does not contain the classical cadherin CAR sequence His-Ala-Val (HAV). As used herein, a "cadherin repeat" refers to an amino acid sequence that is approximately 110 amino acid residues in length (generally 100 to 120 residues, preferably 105 to 115 residues), comprises an extracellular domain, and contains three calcium binding motifs (DXD, XDXE and DXXDX; SEQ ID NOs: 4 and 5, respectively) in the same order and in approximately the same position. The presence of an extracellular domain may generally be determined using well known techniques, such as the presence of one or more of: a hydrophilic sequence, a region that is recognized by an antibody, a region that is cleaved by trypsin and/or a potential glycosylation site with the glycosylation motif Asn-X-Ser/Thr. The second calcium binding motif commonly has the sequence LDRE (SEQ ID NO:6), although variants of this sequence with conservative substitutions are also observed, including MDRE (SEQ ID NO:7), LDFE (SEQ ID NO:8), LDYE (SEQ ID NO:9), IDRE (SEQ ID NO:10), VDRE (SEQ ID NO:11) and IDFE (SEQ ID NO:12). Within most cadherin repeats, the third calcium binding motif has the sequence [L,I,V]-X-[L,I,V]-X-D-X-N-D-[N,H]-X-P (SEQ ID NO:13), wherein residues indicated in brackets may be any one of the recited residues. A preferred third calcium binding motif has the sequence DXNDN (SEQ ID NO:14), although one or both of the D residues may be replaced by an E. Homology among cadherin repeats is generally at least 20%, preferably at least 30%, as determined by the ALIGN algorithm (Myers and Miller, *CABIOS* 4:11–17, 1988). Most OB-cadherins comprise at least five cadherin repeats, along with a hydrophobic domain that transverses the plasma membrane and, optionally, one or more cytoplasmic domains.

Antimetastatic Agents

Within the context of the present invention, the term "antimetastatic agent" refers to a molecule comprising at least one of the following components:

(a) a linear or cyclic peptide sequence that is at least 50% identical to an OB-cadherin CAR sequence (i.e., an OB-cadherin CAR sequence or an analogue thereof that retains at least 50% sequence identity);

(b) a mimetic (e.g., peptidomimetic or small molecule mimic) of an OB-cadherin CAR sequence;

(c) a substance, such as an antibody or antigen-binding fragment thereof, that specifically binds an OB-cadherin CAR sequence; and/or (d) a polynucleotide encoding a polypeptide that comprises an OB-cadherin CAR sequence or analogue thereof.

An antimetastatic agent may consist entirely of one or more of the above elements, or may additionally comprise further peptide and/or non-peptide regions. Additional peptide regions may be derived from an OB-cadherin (preferably an extracellular domain that comprises a CAR sequence) and/or may be heterologous. Within certain preferred embodiments, an antimetastatic agent contains no more than 85 consecutive amino acid residues, and preferably no more than 50 consecutive amino acid residues, present within an OB-cadherin.

An antimetastatic agent is further capable of inhibiting OB-cadherin mediated cell adhesion. Such activity may generally be assessed using, for example, representative assays provided herein. In general, an antimetastatic agent should inhibit OB-cadherin mediated cell adhesion with an activity that is not substantially diminished relative to the full length OB-cadherin (i.e. the antimetastatic agent inhibits cell adhesion at least as well as soluble OB-cadherin, when contacted with cells that express OB-cadherin). Certain antimetastatic agents further inhibit cell adhesion mediated by a different adhesion molecule.

An OB-cadherin CAR sequence, as used herein, is an amino acid sequence that is present in a naturally occurring OB-cadherin and that is capable of detectably modulating an OB-cadherin-mediated function, such as cell adhesion, as described herein. In other words, contacting an OB-cadherin-expressing cell with a peptide comprising a CAR sequence results in a detectable change in OB-cadherin-mediated cell adhesion using at least one of the representative assays provided herein. CAR sequences are generally recognized in vivo by an OB-cadherin or other adhesion molecule (i.e., a molecule that mediates cell adhesion via a receptor on the cell surface), and are necessary for maximal heterophilic and/or homophilic interaction. CAR sequences may be of any length, but generally comprise at least three amino acid residues, preferably 4–16 amino acid residues, and more preferably 5–9 amino acid residues. A peptide antimetastatic agent may comprise any number of amino acid residues, but preferred agents comprise 3–50 residues, preferably 4–16 residues.

It has been found, within the context of the present invention, that certain OB-cadherin CAR sequences share the consensus sequence:

Aaa-Phe-Baa-Ile/Leu/Val-Asp/Asn/Glu-Caa-Daa-Ser/Thr/Asn-Gly    (SEQ ID NO:15)

Within the consensus sequence, Aaa, Baa, Caa and Daa indicate independently selected amino acid residues; "Ile/Leu/Val" indicates an amino acid that is isoleucine, leucine or valine; "Asp/Asn/Glu" indicates an amino acid that is aspartic acid, asparagine or glutamic acid; and "Ser/Thr/Asn" indicates an amino acid that is serine, threonine or asparagine. Representative OB-cadherin CAR sequences are provided within Table I. CAR sequences specifically provided herein further include portions of such representative CAR sequences, as well as longer polypeptides that comprise at least a portion of such sequences. Additional OB-cadherin CAR sequences may be identified based on sequence homology to the OB-cadherin CAR sequences provided herein, and based on the ability of a peptide comprising such a sequence to modulate OB-cadherin-mediated cell adhesion within a representative assay provided herein. Within certain embodiments, an antimetastatic agent comprises at least three consecutive residues, preferably at least five consecutive residues and more preferably at least seven consecutive residues, of an OB-cadherin CAR sequence that satisfies the above consensus sequence.

TABLE I

Representative OB-Cadherin CAR Sequences

| Cadherin | CAR Sequence |
|---|---|
| Human OB-cadherin EC1 | FFVIEEYTG (SEQ ID NO:50) |
| Human OB-cadherin EC1 | IFVIDDKSG (SEQ ID NO:64) |
| Human OB-cadherin EC2 | YFSVEAQTG (SEQ ID NO:78) |

OB-cadherin CAR sequences are generally physically located within the cadherin molecule in or near the binding site of an adhesion molecule (i.e., within 10 amino acids, and preferably within 5 amino acids, of such a binding site). The location of a binding site may generally be determined using well known techniques, such as evaluating the ability of a portion of the OB-cadherin to bind to another OB-cadherin molecule. Any standard binding assay may be employed for such an evaluation. Recognition of a CAR sequence by OB-cadherin results in a measurable effect on cell adhesion. Peptides comprising a CAR sequence generally inhibit such a function.

Certain preferred OB-cadherin CAR sequences comprise 3–9 amino acid residues of a sequence provided in Table I. For example, a CAR sequence may comprise 3, 4 or 5 residues of a 9 amino acid sequence in Table I. In general, an OB-cadherin CAR sequence comprises at least the sequence EEY, DDK or EAQ. Within certain embodiments, a CAR sequence may include at least residues 5–7 of a sequence in Table I.

Representative OB-cadherin CAR sequences comprise one or more of the peptide sequences DDK, IDDK (SEQ ID NO:37) DDKS (SEQ ID NO:38), VIDDK (SEQ ID NO:39), IDDKS (SEQ ID NO:40), VIDDKS (SEQ ID NO:41), DDKSG (SEQ ID NO:42), IDDKSG (SEQ ID NO:43), VIDDKSG (SEQ ID NO:44), FVIDDK (SEQ ID NO:45), FVIDDKS (SEQ ID NO:46), FVIDDKSG (SEQ ID NO:47), IFVIDDK (SEQ ID NO:48), IFVIDDKS (SEQ ID NO:49), IFVIDDKSG (SEQ ID NO:50), EEY, IEEY (SEQ ID NO:51), EEYT (SEQ ID NO:52), VIEEY (SEQ ID NO:53), IEEYT (SEQ ID NO:54), VIEEYT (SEQ ID NO:55), IEEYTG (SEQ ID NO:57), IEEYTG (SEQ ID NO:56), VIEEYTG (SEQ ID NO:58), FVIEEY (SEQ ID NO:59), FVIEEYT (SEQ ID NO:60), FVIEEYTG (SEQ ID NO:61), FFVIEEY (SEQ ID NO:62), FFVIEEYT (SEQ ID NO:63), FFVIEEYTG (SEQ ID NO:64), EAQ, VEAQ (SEQ ID NO:65), EAQT (SEQ ID NO:66), SVEAQ (SEQ ID NO:67), VEAQT (SEQ ID NO:68), SVEAQT (SEQ ID NO:69), EAQTG (SEQ ID NO:70), VEAQTG (SEQ ID NO:71), SVEAQTG (SEQ ID NO:72), FSVEAQ (SEQ ID NO:73), FSVEAQT (SEQ ID NO:74), FSVEAQTG (SEQ ID NO:75), YFSVEAQ (SEQ ID NO:76), YFSVEAQT (SEQ ID NO:77) or YFSVEAQTG (SEQ ID NO:78). Linear peptides having such sequences may be modified at the N- and/or C-termini, as in the peptides N-Ac-IFVIDDKSG-NH$_2$ (SEQ ID NO:50), N-Ac-FFVIEEYTG-NH$_2$ (SEQ ID NO:64) and N-Ac-YFSVEAQTG-NH$_2$ (SEQ ID NO:78).

To enhance specificity for OB-cadherin, an antimetastatic agent may contain a greater number of consecutive residues derived from OB-cadherin. In addition, further flanking sequences may be included to enhance specificity. Such flanking sequences may be identified based on the sequences provided in FIG. 1, or based on published sequences. To achieve specificity (i.e., modulation of OB-cadherin mediated cell adhesion that is enhanced relative to the modulation of a function mediated by a different cadherin), the addition of 2 to 5 flanking residues (preferably at least one residue on either side of the CAR sequence) is generally sufficient. Specificity may be evaluated using assays for the ability to inhibit functions mediated by particular cadherins, as described herein.

As noted above, antimetastatic agents as described herein may comprise an analogue or mimetic of an OB-cadherin CAR sequence. An analogue generally retains at least 50% identity to a native OB-cadherin CAR sequence, and inhibits OB-cadherin-mediated cell adhesion as described herein. Such analogues preferably contain at least three consecutive residues of, and more preferably at least five consecutive residues of, an OB-cadherin CAR sequence. An analogue may contain any of a variety of amino acid substitutions, additions, insertions, deletions and/or modifications (e.g., side chain modifications). Preferred amino acid substitutions are conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of an OB-cadherin CAR sequence analogue is the ability to modulate an OB-cadherin-mediated function, which may be evaluated using the representative assays provided herein.

A mimetic is a non-peptidyl compound that is conformationally similar to an OB-cadherin CAR sequence, such that it modulates OB-cadherin-mediated cell adhesion as described below. Such mimetics may be designed based on techniques that evaluate the three dimensional structure of the peptide. For example, Nuclear Magnetic Resonance spectroscopy (NMR) and computational techniques may be used to determine the conformation of an OB-cadherin CAR sequence. NMR is widely used for structural analyses of both peptidyl and non-peptidyl compounds. Nuclear Overhauser Enhancements (NOE's), coupling constants and chemical shifts depend on the conformation of a compound. NOE data provides the interproton distance between protons through space and can be used to calculate the lowest energy conformation for the OB-cadherin CAR sequence. This information can then be used to design mimetics of the preferred conformation. Linear peptides in solution exist in many conformations. By using conformational restriction techniques it is possible to fix the peptide in the active conformation. Conformational restriction can be achieved by i) introduction of an alkyl group such as a methyl which sterically restricts free bond rotation; ii) introduction of unsaturation which fixes the relative positions of the terminal and geminal substituents; and/or iii) cyclization, which fixes the relative positions of the sidechains. Mimetics may be synthesized where one or more of the amide linkages has been replaced by isosteres, substituents or groups which have the same size or volume such as —CH$_2$NH—, —CSNH—, —CH$_2$S—, —CH=CH—, —CH$_2$CH$_2$—, —CONMe— and others. These backbone amide linkages can also be part of a ring structure (e.g., lactam). Mimetics may be designed where one or more of the side chain functionalities of the OB-cadherin CAR sequence are replaced by groups that do not necessarily have the same size or volume, but have similar chemical and/or physical properties which produce similar biological responses. Other mimetics may be small molecule mimics, which may be readily identified from small molecule libraries, based on the three-dimensional structure of the CAR sequence. It should be understood that, within embodiments described below, an analogue or mimetic may be substituted for an OB-cadherin CAR sequence.

Antimetastatic agents, or peptide portions thereof, may be linear or cyclic peptides. The term "cyclic peptide," as used herein, refers to a peptide or salt thereof that comprises (1) an intramolecular covalent bond between two non-adjacent residues and (2) at least one OB-cadherin CAR sequence or an analogue thereof. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. One or more OB-cadherin CAR sequences, or an analogue or mimetic thereof, may be incorporated into a cyclic peptide, with or without one or more other adhesion molecule binding sites. Additional adhesion molecule binding sites are described in greater detail below.

The size of a cyclic peptide ring generally ranges from 5 to about 15 residues, preferably from 5 to 10 residues. Additional residue(s) may be present on the N-terminal and/or C-terminal side of an OB-cadherin CAR sequence, and may be derived from sequences that flank an OB-cadherin CAR sequence, with or without amino acid substitutions and/or other modifications. Alternatively, additional residues present on one or both sides of the CAR sequence(s) may be unrelated to an endogenous sequence (e.g., residues that facilitate cyclization, purification or other manipulation and/or residues having a targeting or other function).

Within certain embodiments, an antimetastatic agent may comprise a cyclic peptide that contains an OB-cadherin CAR sequence as provided in Table I (or a portion of such a CAR sequence). Certain cyclic peptides have the formula:

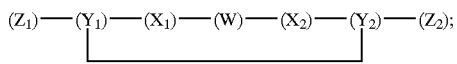

Within this formula, W is a tripeptide selected from the group consisting of EEY, DDK and EAQ; $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; $Y_1$ and $Y_2$ are independently selected from the group consisting of amino acid residues, and wherein a covalent bond is formed between residues $Y_1$ and $Y_2$; and $Z_1$ and $Z_2$ are optional, and if present, are independently selected from the group consisting of amino acid residues and combinations thereof in which the residues are linked by peptide bonds.

Cyclic peptides may comprise any of the above CAR sequence(s). Such cyclic peptides may be used as antimetastatic agents without modification, or may be incorporated into an antimetastatic agent. For example, cyclic peptides may comprise any of the above OB-cadherin CAR sequence(s). Representative cyclic peptides include CDDKC (SEQ ID NO:79), CIDDKC (SEQ ID NO:80), CDDKSC (SEQ ID NO:81), CVIDDKC (SEQ ID NO:82), CIDDKSC (SEQ ID NO:83), CVIDDKSC (SEQ ID NO:84), CDDKSGC (SEQ ID NO:85), CIDDKSGC (SEQ ID NO:86), CVIDDKSGC (SEQ ID NO:87), CFVIDDKC (SEQ ID NO:88), CFVIDDKSC (SEQ ID NO:89), CFVIDDKSGC (SEQ ID NO:90), CIFVIDDKC (SEQ ID NO:91), CIFVIDDKSC (SEQ ID NO:92), CIFVIDDKSGC (SEQ ID NO:93), DDDKK (SEQ ID NO:94), DIDDKK (SEQ ID NO:95), DVIDDKK (SEQ ID NO:96), DFVIDDKK (SEQ ID NO:97), DIFVIDDKK (SEQ ID NO:98), EDDKK (SEQ ID NO:99), EIDDKK (SEQ ID NO:100), EVIDDKK (SEQ ID NO:101), EFVIDDKK (SEQ ID NO:102), EIFVIDDKK (SEQ ID NO:103), FVIDDK (SEQ ID NO:104), FVIDDKS (SEQ ID NO:105), FVIDDKSG (SEQ ID NO:106), KDDKD (SEQ ID NO:107), KIDDKD (SEQ ID NO:108), KDDKSD (SEQ ID NO:109), KVIDDKD (SEQ ID NO:110), KIDDKSD(SEQ ID NO:111), KVIDDKSD (SEQ ID NO:112), KDDKSGD (SEQ ID NO:113), KIDDKSGD (SEQ ID NO:114), KVIDDKSGD (SEQ ID NO:115), KFVIDDKD (SEQ ID NO:116), KFVIDDKSD (SEQ ID NO:117), KFVIDDKSGD (SEQ ID NO:118), KIFVIDDKD (SEQ ID NO:119), KIFVIDDKSD (SEQ ID NO:120), KIFVIDDKSGD (SEQ ID NO:121), VIDDK (SEQ ID NO:122), IDDKS (SEQ ID NO:123), VIDDKS (SEQ ID NO:124), VIDDKSG (SEQ ID NO:125), DDKSG (SEQ ID NO:126), IDDKSG (SEQ ID NO:127), IFVIDDK (SEQ ID NO:128), IFVIDDKS (SEQ ID NO:129), IFVIDDKSG (SEQ ID NO:130), KDDKE (SEQ ID NO:131), KIDDKE (SEQ ID NO:132), KDDKSE (SEQ ID NO:133), KVIDDKE (SEQ ID NO:134), KIDDKSE (SEQ ID NO:135), KVIDDKSE (SEQ ID NO:136), KDDKSGE (SEQ ID NO:137), KIDDKSGE (SEQ ID NO:138), KVIDDKSGE (SEQ ID NO:139), KFVIDDKE (SEQ ID NO:140), KFVIDDKSE (SEQ ID NO:141), KFVIDDKSGE (SEQ ID NO:142), KIFVIDDKE (SEQ ID NO:143), KIFVIDDKSE (SEQ ID NO:144), KIFVIDDKSGE (SEQ ID NO:145), CEEYC (SEQ ID NO:146), CIEEYC (SEQ ID NO:147), CEEYTC (SEQ ID NO:148), CVIEEYC (SEQ ID NO:149), CIEEYTC (SEQ ID NO:150), CVIEEYTC (SEQ ID NO:151), CEEYTGC (SEQ ID NO:152), CIEEYTGC (SEQ ID NO:153), CVIEEYTGC (SEQ ID NO:154), CFVIEEYC (SEQ ID NO:155), CFVIEEYTC (SEQ ID NO:156), CFVIEEYTGC (SEQ ID NO:157), CFFVIEEYC (SEQ ID NO:158), CFFVIEEYTC (SEQ ID NO:159), CFFVIEEYTGC (SEQ ID NO:160), KEEYD (SEQ ID NO:161), KIEEYD (SEQ ID NO:162), KEEYTD (SEQ ID NO:163), KVIEEYD (SEQ ID NO:164), KIEEYTD (SEQ ID NO:165), KVIEEYTD (SEQ ID NO:166), KEEYTGCD (SEQ ID NO:167), KIEEYTGD (SEQ ID NO:168), KVIEEYTGD (SEQ ID NO:169), KFVIEEYD (SEQ ID NO:170), KFVIEEYTD (SEQ ID NO:171), KFVIEEYTGD (SEQ ID NO:172), KFFVIEEYD (SEQ ID NO:173), KFFVIEEYTD (SEQ ID NO:174), KFFVIEEYTGD (SEQ ID NO:175), EEEYK (SEQ ID NO:176), EIEEYK (SEQ ID NO:177), EEEYTK (SEQ ID NO:178), EVIEEYK (SEQ ID NO:179), EIEEYTK (SEQ ID NO:180), EVIEEYTK (SEQ ID NO:181), EEEYTGK (SEQ ID NO:182), EIEEYTGK (SEQ ID NO:183), EVIEEYTGK (SEQ ID NO:184), EFVIEEYK (SEQ ID NO:185), EFVIEEYTK (SEQ ID NO:186), EFVIEEYTGK (SEQ ID NO:187), EFFVIEEYK (SEQ ID NO:188), EFFVIEEYTK (SEQ ID NO:189), EFFVIEEYTGK (SEQ ID NO:190), DCEEYK (SEQ ID NO:191), DIEEYCK (SEQ ID NO:192), DEEYTK (SEQ ID NO:193), DVIEEYK (SEQ ID NO:194), DIEEYTK (SEQ ID NO:195), DVIEEYTK (SEQ ID NO:196), DEEYTGK (SEQ ID NO:197), DIEEYTGK (SEQ ID NO:198), DVIEEYTGK (SEQ ID NO:199), DFVIEEYK (SEQ ID NO:200), DFVIEEYTK (SEQ ID NO:201), DFVIEEYTGK (SEQ ID NO:202), DFFVIEEYK (SEQ ID NO:7203), DFFVIEEYTK (SEQ ID NO:204), DFFVIEEYTGK (SEQ ID NO:205), KEEYE (SEQ ID NO:206), KIEEYE (SEQ ID NO:207), KEEYTE (SEQ ID NO:208), KVIEEYE (SEQ ID NO:209), KIEEYTE (SEQ ID NO:210), KVIEEYTE (SEQ ID NO:211), KEEYTGE (SEQ ID NO:212), KIEEYTGE (SEQ ID NO:213), KVIEEYTGE (SEQ ID NO:214), KFVIEEYE (SEQ ID NO:215), KFVIEEYTE (SEQ ID NO:216), KFVIEEYTGE (SEQ ID NO:217), KFFVIEEYE (SEQ ID NO:218), KFFVIEEYTE (SEQ ID NO:219), KFFVIEEYTGE (SEQ ID NO:220), VIEEY (SEQ ID NO:221), IEEYT (SEQ ID NO:222), VIEEYT (SEQ ID NO:223), EEYTG (SEQ ID NO:224), IEEYTG (SEQ ID NO:225), VIEEYTG (SEQ ID NO:226), FVIEEY (SEQ ID NO:227), FVIEEYT (SEQ ID NO:228), FVIEEYTG (SEQ ID NO:229), FFVIEEY (SEQ ID NO:230), FFVIEEYT (SEQ ID NO:231), FFVIEEYTG (SEQ ID NO:232), CEAQC (SEQ ID NO:233), CVEAQC (SEQ ID NO:234), CEAQTC (SEQ ID NO:235), CSVEAQC (SEQ ID NO:236), CVEAQTC (SEQ ID NO:237), CSVEAQTC (SEQ ID NO:238), CEAQTGC (SEQ ID NO:239), CVEAQTGC (SEQ ID NO:240), CSVEAQTGC (SEQ ID NO:241), CFSVEAQC (SEQ ID NO:242), CFSVEAQTC (SEQ ID NO:243), CFSVEAQTGC (SEQ ID NO:244), CYFSVEAQC (SEQ ID NO:245), CYFSVEAQTC (SEQ ID NO:246), CYFSVEAQTGC (SEQ ID NO:247), KEAQD (SEQ ID NO:248), KVEAQD (SEQ ID NO:249), KEAQTD (SEQ ID NO:250), KSVEAQD (SEQ ID NO:251), KVEAQTD (SEQ ID NO:252), KSVEAQTD (SEQ ID NO:253), KEAQTGD (SEQ ID NO:254), KVEAQTGD (SEQ ID NO:255), KSVEAQTGD (SEQ ID NO:256), KFSVEAQD (SEQ ID NO:257), KFSVEAQTD (SEQ ID NO:258), KFSVEAQTGD (SEQ ID NO:259), KYFSVEAQD (SEQ ID NO:260), KYFSVEAQTD (SEQ ID NO:261), KYFSVEAQTGD (SEQ ID NO:262), EEAQK (SEQ ID NO:263), EVEAQK (SEQ ID NO:264), EEAQTK (SEQ ID NO:265), ESVEAQK (SEQ ID NO:266), EVEAQTK (SEQ ID NO:267), ESVEAQTK (SEQ ID NO:268), EEAQTGK (SEQ ID NO:269), EVEAQTGK (SEQ ID NO:270), ESVEAQTGK (SEQ ID NO:271), EFSVEAQK (SEQ ID NO:272), EFSVEAQTK (SEQ ID NO:273), EFSVEAQTGK (SEQ ID NO:274), EYFSVEAQK (SEQ ID NO:275), EYFSVEAQTK (SEQ ID NO:276), EYFSVEAQTGK (SEQ ID NO:277), DEAQK (SEQ ID NO:278), DVEAQK (SEQ ID NO:279), DEAQTK (SEQ ID NO:280), DSVEAQK (SEQ ID NO:281), DVEAQTK (SEQ ID NO:282), DSVEAQTK (SEQ ID NO:283), DEAQTGK (SEQ ID NO:284), DVEAQTGK (SEQ ID NO:285), DSVEAQTGK (SEQ ID NO:286), DFSVEAQK (SEQ ID NO:287), DFSVEAQTK (SEQ ID NO:288), DFSVEAQTGK (SEQ ID NO:289), DYFSVEAQK (SEQ ID NO:290), DYFSVEAQTK (SEQ ID NO:291), DYFSVEAQTGK (SEQ ID NO:292), KEAQE (SEQ ID NO:293), KVEAQE (SEQ ID NO:294), KEAQTE (SEQ ID NO:295), KSVEAQE (SEQ ID NO:296), KVEAQTE (SEQ ID NO:297), KSVEAQTE (SEQ ID NO:298), KEAQTGE (SEQ ID NO:299), KVEAQTGE (SEQ ID NO:300), KSVEAQTGE (SEQ ID NO:301), KFSVEAQE (SEQ ID NO:302), KFSVEAQTE (SEQ ID NO:303), KFSVEAQTGE (SEQ ID NO:304), KYFSVEAQE (SEQ ID NO:305), KYFSVEAQTE (SEQ ID NO: 306), KYFSVEAQTGE (SEQ ID NO:307), SVEAQ (SEQ ID NO:308), VEAQT (SEQ ID NO:309), SVEAQT (SEQ ID NO:310), EAQTG (SEQ ID NO:31), VEAQTG (SEQ ID NO:312), SVEAQTG (SEQ ID NO:313), FSVEAQ (SEQ ID NO:314), FSVEAQT (SEQ ID NO:315), FSVEAQTG (SEQ ID NO:316), YFSVEAQ (SEQ ID NO:317), YFSVEAQT (SEQ ID NO:318) and YFSVEAQTG (SEQ ID NO:319). Within the context of the present invention, underlined sequences are cyclized using any suitable method, as described herein.

As noted above, certain preferred antimetastatic agents comprise a peptide (containing an OB-cadherin CAR sequence or an analogue thereof) in which at least one terminal amino acid residue is modified (e.g., the N-terminal amino group is modified by, for example, acetylation or alkoxybenzylation and/or an amide or ester is formed at the C-terminus). It has been found, within the context of the present invention, that the addition of at least one such group to a linear or cyclic peptide antimetastatic agent may improve the ability of the agent to modulate an OB-cadherin-mediated function. Certain preferred antimetastatic agents contain modifications at the N- and C-terminal residues, such as N-Ac-IFVIDDKSG-NH$_2$ (SEQ ID NO:50).

Within certain embodiments, cyclic peptides that contain small CAR sequences (e.g., three residues without significant flanking sequences) may be preferred. Such peptides may contain an N-acetyl group and a C-amide group (e.g., the 5-residue ring N-Ac-CDDKC-NH$_2$ (SEQ ID NO:79) or N-Ac-KDDKD-NH$_2$ (SEQ ID NO:107)). Small cyclic peptides may generally be used to specifically modulate adhesion of cancer cells by topical administration or by systemic administration, with or without linking a targeting agent to the peptide, as discussed below. Certain representative cyclic peptides comprising an OB-cadherin CAR sequence are shown in FIGS. 2A–2C.

An antimetastatic agent may contain one OB-cadherin CAR sequence, or multiple CAR sequences that are adjacent to one another (i.e., without intervening sequences) or in close proximity (i.e., separated by peptide and/or non-peptide linkers to give a distance between the OB-cadherin CAR sequences that ranges from about 0.1 to 400 nm). A linker may be any molecule (including peptide and/or non-peptide sequences) that does not contain a CAR sequence and that can be covalently linked to at least two peptide sequences. Using a linker, CAR sequence-containing peptides and other peptide or protein sequences may be joined end-to-end (i.e., the linker may be covalently attached to the carboxyl or amino group of each peptide sequence), and/or via side chains. One linker that can be used for such purposes is H$_2$N(CH$_2$)$_n$CO$_2$H, or derivatives thereof, where n ranges from 1 to 4. Other linkers that may be used will be apparent to those of ordinary skill in the art. Peptide and non-peptide linkers may generally be incorporated into an antimetastatic agent using any appropriate method known in the art.

An antimetastatic agent as described herein may additionally comprise one or more CAR sequences for one or more different adhesion molecules (including, but not limited to, other CAMs) and/or one or more substances, such as antibodies or fragments thereof, that bind to such sequences. Linkers may, but need not, be used to separate such CAR sequence(s) and/or antibody sequence(s) from the CAR sequence(s) and/or each other. Such antimetastatic agents may generally be used within methods in which it is desirable to simultaneously disrupt a function mediated by multiple adhesion molecules. As used herein, an "adhesion molecule" is any molecule that mediates cell adhesion via a receptor on a cell's surface. Adhesion molecules include cell adhesion proteins (e.g., other members of the cadherin gene superfamily, such as N-cadherin and E-cadherin); occludin; claudin; integrins; extracellular matrix proteins such as laminin, fibronectin, collagens, vitronectin, entactin and tenascin; and members of the immunoglobulin supergene family, such as N-CAM, PE-CAM, CEA, L1 or junction associated molecule (JAM; see Martin-Padura et al., *J. Cell Biol.* 142:117–127, 1998). Preferred CAR sequences for inclusion within an antimetastatic agent include the classical cadherin CAR sequence His-Ala-Val (HAV); Arg-Gly-Asp (RGD), which is bound by integrins (see Cardarelli et al., *J. Biol. Chem.* 267:23159–64, 1992); Tyr-Ile-Gly-Ser-Arg (YIGSR; SEQ ID NO:16), which is bound by α6β1 integrin; the cadherin-5 CAR sequence DAE; the cadherin-6 CAR sequences EEY, NEN, ESE and DSG; the N-CAM CAR sequence KYSFNYDGSE (SEQ ID NO:17; see Rao et al., *J. Cell. Biol.* 118:937–949, 1992); an occludin CAR sequence (LYHY; SEQ ID NO:18), a claudin CAR sequence (such as IYSY, TSSY, VTAF and VSAF; SEQ ID NOs:19–22) or a JAM CAR sequence (SFTIDPKSG (SEQ ID NO:32) or DPK). Using linkers, such antimetastatic agents may form linear or branched structures.

The total number of CAR sequences (including the OB-cadherin CAR sequence, with or without other CAR sequences derived from one or more different adhesion molecules) present within an antimetastatic agent may range from 1 to a large number, such as 100, preferably from 1 to 10, and more preferably from 1 to 5. Peptide antimetastatic agents comprising multiple CAR sequences typically contain from 6 (e.g., DDK-HAV) to about 1000 amino acid residues, preferably from 6 to 50 residues. When non-peptide linkers are employed, each CAR sequence of the antimetastatic agent is present within a peptide that generally ranges in size from 3 to 50 residues in length, preferably from 4 to 25 residues, and more preferably from 5 to 15 residues.

As noted above, antimetastatic agents may be polypeptides or salts thereof, containing only amino acid residues linked by peptide bonds, or may contain non-peptide regions, such as linkers. Peptide regions of an antimetastatic agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations, and the corresponding D-amino acids are designated by a lower case one letter symbol.

An antimetastatic agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with an antimetastatic agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Peptide antimetastatic agents (and peptide portions of antimetastatic agents) as described herein may be synthesized by methods well known in the art, including chemical synthesis and recombinant DNA methods. For antimetastatic agents up to about 50 residues in length, chemical synthesis may be performed using solution or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N-Ac and C-terminal amide groups are represented by -NH$_2$:

i) N-Ac-Cys-Asp-Asp-Lys-Cys-NH$_2$ (SEQ ID NO:79)
ii) N-Ac-Cys-Ile-Asp-Asp-Lys-Ser-Gly-Cys-NH$_2$ (SEQ ID NO:86)
iii) N-Ac-Cys-Ile-Asp-Asp-Lys-Cys-NH$_2$ (SEQ ID NO:80)
iv) N-Ac-Cys-Asp-Asp-Lys-Ser-Cys-NH$_2$ (SEQ ID NO:81)
v) N-Ac-Cys-Ile-Asp-Asp-Lys-Ser-Cys-NH$_2$ (SEQ ID NO:83)
vi) N-Ac-Cys-Asp-Asp-Lys-Ser-Cys-OH (SEQ ID NO:81)
vii) H-Cys-Ile-Asp-Asp-Lys-Ser-Cys-NH$_2$ (SEQ ID NO:83)
viii) N-Ac-Cys-Asp-Asp-Lys-Pen-NH$_2$ (SEQ ID NO:23)
ix) N-Ac-Cys-Phe-Val-Ile-Asp-Asp-Lys-Ser-Gly-Cys-NH$_2$ (SEQ ID NO:90)
x) N-Ac-Cys-Ile-Phe-Val-Ile-Asp-Asp-Lys-Ser-Gly-Cys-NH$_2$ (SEQ ID NO:93)
xi) N-Ac-Ile-Tmc-Val-Ile-Asp-Asp-Lys-Ser-Cys-Glu-NH$_2$ (SEQ ID NO:24)
xii) N-Ac-Ile-Pmc-Val-Ile-Asp-Asp-Lys-Ser-Gly-Cys-NH$_2$ (SEQ ID NO:25)
xiii) Mpr-Val-Ile-Asp-Asp-Lys-Ser-Gly-Cys-NH$_2$ (SEQ ID NO:26)
xiv) Pmp-Val-Ile-Asp-Asp-Lys-Ser-Gly-Cys-NH$_2$ (SEQ ID NO: 27)

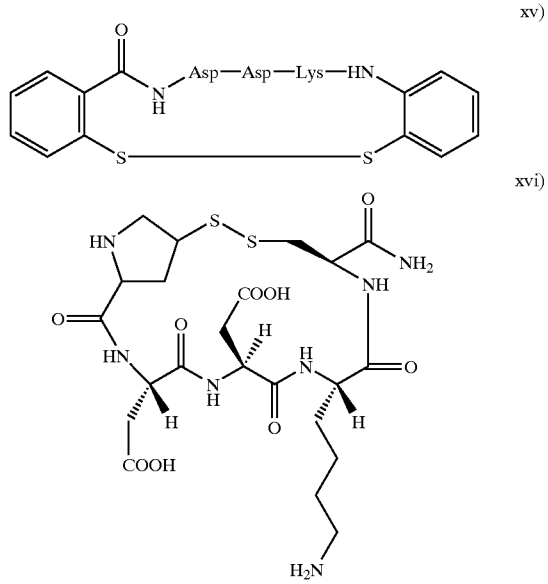

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization). One such cyclic peptide is <u>IDDKSG</u> (SEQ ID NO:127) with or without an N-terminal acetyl group and/or a C-terminal amide. Within another such embodiment, the linear peptide comprises a D-amino acid (e.g., <u>DDKsS</u>; SEQ ID NO:28). Alternatively, cyclization may be accomplished by linking one terminus and a residue side chain or using two side chains, as in <u>KDDKD</u> (SEQ ID NO:107) or <u>KIDDKSGD</u> (SEQ ID NO:114), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

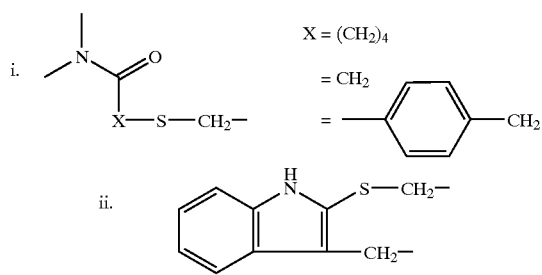

Cyclization may also be achieved using $\delta_1,\delta_1$-Ditryptophan (i.e., Ac-Trp-Gly-Gly-Trp-OMe) (SEQ ID NO:29), as shown below:

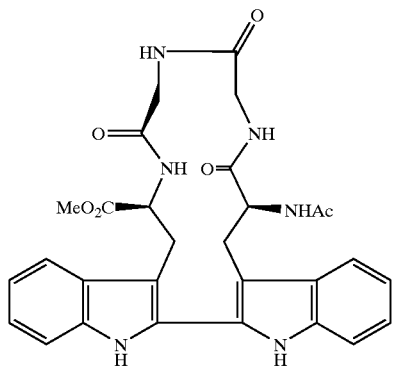

Representative structures of cyclic peptides comprising OB-cadherin CAR sequences are provided in FIGS. 2A–2C. The structures and formulas recited herein are provided solely for the purpose of illustration, and are not intended to limit the scope of the cyclic peptides described herein.

For longer antimetastatic agents, recombinant methods are preferred for synthesis. Within such methods, all or part of an antimetastatic agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an OB-cadherin or other adhesion molecule, or may encode a peptide comprising an OB-cadherin analogue or an antibody fragment that specifically binds to an OB-cadherin CAR sequence. Such DNA sequences may be prepared based on known cDNA or genomic sequences, or from sequences isolated by screening an appropriate library with probes designed based on the sequences of known OB-cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired antimetastatic agent, an endogenous cadherin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the antimetastatic agent.

As noted above, polynucleotides may also function as antimetastatic agents. In general, such polynucleotides should be formulated to permit expression of a polypeptide antimetastatic agent following administration to a mammal. Such formulations are particularly useful for therapeutic purposes, as described below. Those of ordinary skill in the art will appreciate that there are many ways to achieve expression of a polynucleotide within a mammal, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transfected cells) and/or a targeting moiety, such as a gene that encodes a ligand for a receptor on a specific target cell, to render the vector target specific. Targeting may also be accomplished using an antibody, by methods known to those of ordinary skill in the art. Other formulations for polynucleotides for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

As noted above, an antimetastatic agent may additionally, or alternatively, comprise a substance such as an antibody or antigen-binding fragment thereof, that specifically binds to an OB-cadherin CAR sequence. As used herein, a substance is said to "specifically bind" to an OB-cadherin CAR sequence (with or without flanking amino acids) if it reacts at a detectable level with a peptide containing that sequence, and does not react detectably with peptides containing a different CAR sequence or a sequence in which the order of amino acid residues in the cadherin CAR sequence and/or flanking sequence is altered. Such antibody binding properties may generally be assessed using an ELISA, which may be readily performed by those of ordinary skill in the art and is described, for example, by Newton et al., *Develop. Dynamics* 197:1–13, 1993.

Polyclonal and monoclonal antibodies may be raised against a CAR sequence using conventional techniques. See, e.g., Harlow and Lane, *Antibodies: A Laboratory Manual*, Cold Spring Harbor Laboratory, 1988. In one such technique, an immunogen comprising the CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the CAR sequence or antigenic portion thereof coupled to a suitable solid support.

Monoclonal antibodies specific for an OB-cadherin sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the antimetastatic agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation and extraction. Antibodies having the desired activity may generally be identified using immunofluorescence analyses of tissue sections, cell or other samples where the target cadherin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Evaluation of Antimetastatic Agent Activity

Antimetastatic agents as described above are capable of inhibiting OB-cadherin-mediated cell adhesion. An initial screen for such activity may be performed by evaluating the ability of an antimetastatic agent to bind to OB-cadherin using any binding assay known to those of ordinary skill in the art. For example, a Pharmacia Biosensor machine may be used, as discussed in Jonsson et al., *Biotechniques* 11:520–27, 1991. A specific example of a technology that measures the interaction of peptides with molecules can be found in Williams et al., *J. Biol. Chem.* 272, 22349–22354, 1997. Alternatively, real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

By way of example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 $\mu$g/ml) in 10 mM Sodium Acetate, pH 4.0, according to the manufacturer's protocol. Approximately 2100–2600 resonance units (RU) of ligand may be immobilized, corresponding to a concentration of about 2.1–2.6 ng/mm$^2$. The chips may then coated be with OB-cadherin derivatized to biotin. Any non-specifically bound protein is removed.

To determine binding, test analytes (e.g., peptides containing the OB-cadherin CAR sequence) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, an antimetastatic agent binds to OB-cadherin at a detectable level within such as assay. The level of binding is preferably at least that observed for the full length OB-cadherin under similar conditions.

The ability to inhibit OB-cadherin-mediated cell adhesion may be evaluated using any of a variety of in vitro assays.

It has been found, within the context of the present invention, that OB-cadherin is associated with adhesion of certain cancer cells. The ability of an agent to inhibit OB-cadherin mediated cell adhesion may generally be evaluated in vitro by assaying the effect on adhesion between OB-cadherin-expressing cells (i.e., any type of cell that expresses OB-cadherin at a detectable level, using standard techniques such as immunocytochemical protocols (e.g., Blaschuk and Farookhi, *Dev. Biol.* 136:564–567, 1989), such as stromal, osteoblast and/or cancer cells).

In general, an agent is an inhibitor of cell adhesion if contact of the test cells with the antimetastatic agent results in a discernible disruption of cell adhesion, when such cells are plated under standard conditions that, in the absence of antimetastatic agent, permit cell adhesion. In the presence of antimetastatic agent (e.g., 1 mg/mL), disruption of cell adhesion may be determined visually within 24 hours, by observing retraction of the cells from one another and the substratum.

Alternatively, cells that do not naturally express OB-cadherin may be used within such assays. Such cells may be stably transfected with a polynucleotide (e.g., a cDNA) encoding OB-cadherin, such that OB-cadherin is expressed on the surface of the cell. Expression of the cadherin may be confirmed by assessing adhesion of the transfected cells, in conjunction with immunocytochemical techniques using antibodies directed against the cadherin of interest. The stably transfected cells that aggregate, as judged by light microscopy, following transfection express sufficient levels of OB-cadherin. Preferred cells for use in such assays include L cells, which do not detectably adhere and do not express any cadherin (Nagafuchi et al., *Nature* 329:341–343, 1987). Following transfection of L cells with a cDNA encoding OB-cadherin, aggregation is observed (see Okazaki et al., *J. Biol. Chem.* 269:12092–98, 1994). Antimetastatic agents detectably inhibit such aggregation.

Transfection of cells for use in cell adhesion assays may be performed using standard techniques and published OB-cadherin sequences. For example, a sequence of OB-cadherin may be found within references cited herein and in the GenBank database at accession number L34056 (human OB cadherin).

By way of example, an assay for evaluating an antimetastatic agent for the ability to inhibit OB-cadherin mediated cell adhesion may employ MDA-231 human breast cancer cells. According to a representative procedure, the cells may be plated at 10–20,000 cells per 35 mm tissue culture flasks containing DMEM with 5% FCS and subcultured periodically (Sommers et al., *Cell Growth Diffn* 2:365–72, 1991). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to antimetastatic agent at a concentration of, for example, 1 mg/mL for 24 hours. Fresh antimetastatic agent may then be added, and the cells left for an additional 24 hours. Cells may be fixed with 2% paraformaldehyde for 30 minutes and then washed three times with PBS. Coverslips can be mounted and viewed by phase contrast microscopy.

In the absence of antimetastatic agent, MDA-231 cells display an epithelial-like morphology and are well attached to the substratum. MDA-231 cells that are treated with an antimetastatic agent may assume a round shape and become loosely attached to the substratum within 48 hours of treatment with 1 mg/mL of antimetastatic agent.

Antimetastatic Agent Modification and Formulations

An antimetastatic agent as described herein may, but need not, be linked to one or more additional molecules and/or support materials. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Suitable methods for linking an antimetastatic agent to a support material will depend upon the composition of the support and the intended use, and will be readily apparent to those of ordinary skill in the art. Attachment may generally be achieved through noncovalent association, such as adsorption or affinity or via covalent attachment (which may be a direct linkage between an antimetastatic agent and functional groups on the support, or may be a linkage by way of a cross-linking agent). Attachment of an antimetastatic agent by adsorption may be achieved by contact, in a suitable buffer, with a solid support for a suitable amount of time. The contact time varies with temperature, but is generally between about 5 seconds and 1 day, and typically between about 10 seconds and 1 hour. Covalent attachment of an antimetastatic agent to a molecule or solid support may generally be achieved by first reacting the support material with a bifunctional reagent that will also react with a functional group, such as a hydroxyl or amino group, on the antimetastatic agent. A preferred method of generating a linkage is via amino groups using glutaraldehyde. An antimetastatic agent may be linked to cellulose via ester linkages. Similarly, amide linkages may be suitable for linkage to other molecules such as keyhole limpet hemocyanin or other support materials.

Although antimetastatic agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to an antimetastatic agent to facilitate targeting to one or more specific tissues. As used herein, a "targeting agent" may be any substance (such as a compound or cell) that, when linked to an antimetastatic agent enhances the transport of the agent to a target tissue, thereby increasing the local concentration of the antimetastatic agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multi-functional linkers.

For certain embodiments, it may be beneficial to also, or alternatively, link a drug to an antimetastatic agent. As used herein, the term "drug" refers to any bioactive agent intended for administration to a mammal to prevent or treat a disease or other undesirable condition. Drugs include hormones, growth factors, proteins, peptides and other compounds. Drugs include other anticancer or antimetastatic agents.

Antimetastatic agents as described herein may be present within a pharmaceutical composition. A pharmaceutical composition comprises one or more antimetastatic agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more antimetastatic agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, sublingual or intramuscular administration.

For certain embodiments, as discussed below, a pharmaceutical composition may further comprise a modulator of cell adhesion that is mediated by one or more molecules other than OB-cadherin. Such modulators may generally be prepared as described above, using one or more CAR sequences and/or antibodies thereto. Such compositions are particularly useful for situations in which it is desirable to inhibit cell adhesion mediated by multiple cell adhesion molecules, such as other members of the cadherin gene superfamily such as the classical cadherins (e.g., N-cadherin or E-cadherin); nonclassical cadherins (e.g., cadherin-5 or cadherin-6); integrins, occludin, claudin or members of the immunoglobulin superfamily (CEA, PE-CAM, N-CAM, L1 or JAM).

A pharmaceutical composition may also, or alternatively, contain one or more drugs, which may be linked to an antimetastatic agent or may be free within the composition. Virtually any drug may be administered in combination with an antimetastatic agent as described herein. Examples of types of drugs that may be administered with an antimetastatic agent include anticancer drugs (e.g. taxol or mitomycin C) and chemotherapeutic agents.

The compositions described herein may be administered as part of a sustained release formulation (i.e., a formulation such as a capsule or sponge that effects a slow release of antimetastatic agent following administration). Such formulations may generally be prepared using well known technology and administered by, for example, oral, rectal or subcutaneous implantation, or by implantation at the desired target site. Sustained-release formulations may contain an antimetastatic agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of antimetastatic agent release. The amount of antimetastatic agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the antimetastatic agent(s) in an amount sufficient to provide therapeutic and/or prophylactic benefit. Within particularly preferred embodiments of the invention, an antimetastatic agent may be administered at a dosage ranging from 0.001 to 50 mg/kg body weight, preferably from 0.1 to 20 mg/kg, on a regimen of single or multiple daily doses. For topical administration, a cream typically comprises an amount of antimetastatic agent ranging from 0.00001% to 1%, preferably 0.0001% to 0.002%. Fluid compositions typically contain about 10 ng/ml to 5 mg/ml, preferably from about 10 $\mu$g to 2 mg/mL antimetastatic agent. Appropriate dosages may generally be determined using experimental models and/or clinical trials. In general, the use of the minimum dosage that is sufficient to provide effective antimetastatic therapy is preferred.

Antimetastatic Agent Methods of Use

In general, the antimetastatic agents and compositions described herein may be used to block tumor cell adhesion, and to inhibit metastasis of OB-cadherin expressing cancer cells. Such inhibition may be may be achieved by administering an antimetastatic agent to a human or nonhuman patient, using any method that contacts the cancer cells with the antimetastatic agent. Within the methods described herein, one or more antimetastatic agents may generally be administered alone, or within a pharmaceutical composition. A targeting agent may be employed to increase the local concentration of antimetastatic agent at a target site. Alternatively, an antimetastatic agent may be used to remove metastatic cells from blood or bone marrow ex vivo (i.e., from blood or bone marrow obtained from a patient, which may then be returned to the patient following removal of metastatic cells).

Within certain aspects, the present invention provides methods for treating cancer and inhibiting metastasis in a mammal. Metastasis of any cancer in which cancer cells express OB-cadherin may be inhibited. Such cancers include, but are not limited to, carcinoma (e.g., breast and ovarian carcinomas), leukemias (e.g., B-cell chronic lymphocyte leukemia) and melanomas.

Antimetastatic agents may further be designed to disrupt cell adhesion mediated by an adhesion molecule such as cadherin-5, cadherin-6, E-cadherin, N-cadherin, occludin, claudin, N-CAM, PE-CAM, L1, JAM and/or an integrin. For example, such an antimetastatic agent may comprise an OB-cadherin CAR sequence (or analogue or mimetic thereof), optionally in combination with a sequence such as HAV, SHAVSS (SEQ ID NO:30), AHAVDI (SEQ ID NO:31), RGD, YIGSR (SEQ ID NO:16) or a derivative of such a sequence. Preferably, the peptide portion(s) of such antimetastatic agents comprise 6–16 amino acids. Preferred antibody antimetastatic agents include Fab fragments directed against any of the above adhesion molecule CAR sequences. The Fab fragments may be either incorporated into an antimetastatic agent or may be present within a separate modulator that is administered concurrently.

An antimetastatic agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more antimetastatic agents may prevent metastasis of ovarian tumor cells. Other tumors (e.g., bladder tumors, bronchial tumors or tracheal tumors) may be treated by injection of the antimetastatic agent into the cavity. In other instances, the composition may be administered systemically, and targeted to the tumor using any of a variety of specific targeting agents, as described above. Preferably, the tumor is a breast, ovarian, stomach, prostate or kidney tumor. In general, the amount of antimetastatic agent administered varies depending upon the method of administration and the nature of the cancer, but may vary within the ranges identified above. The effectiveness of the cancer treatment or inhibition of metastasis may be evaluated using well known clinical observations, such as monitoring the level of serum tumor markers (e.g., CEA or PSA).

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

Within other aspects, antimetastatic agents may be used to remove metastatic cells from a biological sample, such as blood, bone marrow or a fraction thereof. Such removal may be achieved by contacting a biological sample with an antimetastatic agents under conditions and for a time sufficient to permit OB-cadherin expressing cells to bind to the antimetastatic agent. The OB-cadherin expressing cells that have bound to the antimetastatic agent are then separated from the remainder of the sample. To facilitate this removal, an antimetastatic agent may be linked to a solid support. Preferably, the contact results in the reduction of OB-cadherin expressing cells in the sample to less than 1%, preferably less than 0.1%, of the level prior to contact with the antimetastatic agent. The extent to which such cells have been removed may be readily determined by standard methods such as, for example, qualitative and quantitative PCR analysis, immunohistochemistry and FACS analysis. Following removal of metastatic cells, the biological sample may be returned to the patient using standard techniques.

The following Examples are offered by way of illustration and not by way of limitation.

EXAMPLES

Example 1

Preparation of Representative Antimetastatic Agents

This Example illustrates the solid phase synthesis of representative peptide antimetastatic agents.

The peptides were synthesized on a 431A Applied Biosystems peptide synthesizer using p-Hydroxymethylphenoxymethyl polystyrene (HMP) resin and standard Fmoc chemistry. After synthesis and deprotection, the peptides were de-salted on a Sephadex G-10 column and lyophilized. The peptides were analyzed for purity by analytical HPLC, and in each case a single peak was observed. Peptides were made as stock solutions at 10 to 25 mg/mL in dimethylsulfoxide (DMSO) or water and stored at −20° C. before use.

Example 2

Disruption of Human Breast Cancer Cell Adhesion

This Example illustrates the ability of a representative linear peptide comprising an OB-cadherin CAR sequence to disrupt human breast epithelial cell adhesion.

Figure 3A:
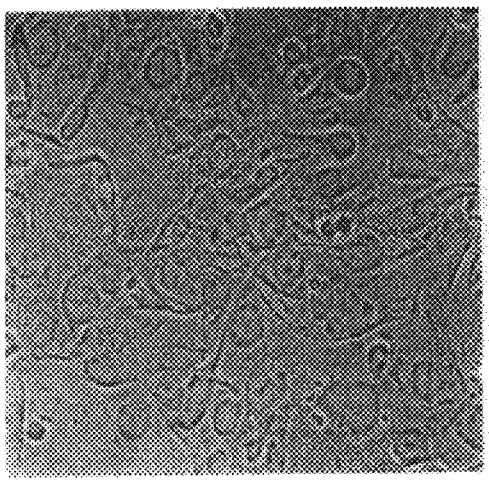
FIGS. 3A–3C are photographs showing cultures of human breast cancer cells in the presence (FIGS. 3B and 3C) and absence (FIG. 3A) of a representative linear peptide antimetastatic agent.
Figure 3B:
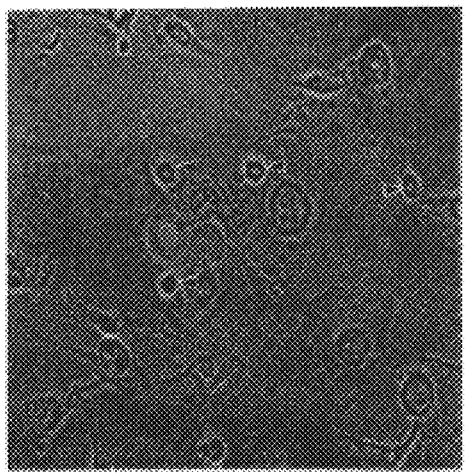
Figure 3C:
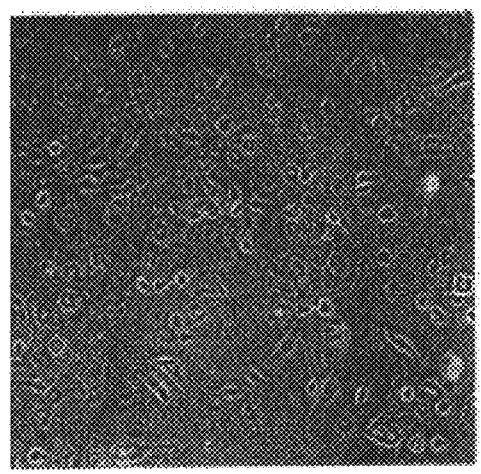

MDA-MB-231 human breast cancer cells (Lombardi Cancer Research Center, Washington, D.C.) were used in these experiments. They express OB-cadherin, but not N-cadherin or E-cadherin. The cells were plated (~50,000 cells) on glass coverslips and cultured for 24 hours in DMEM containing 5% serum. Peptides (N-Ac-IFVIDDKSG-NH$_2$ (SEQ ID NO:50) and H-IFVIDDKSG-OH (SEQ ID NO:50)) were dissolved in sterile water (10 mg/ml), and 100 μl of each peptide stock solution was added to 1 ml of DMEM containing 5% serum. Control cells had 100 μl of water added to the medium. Cells were monitored by phase contrast microscopy. After 24 hours cells were fixed in formaldehyde. After 24 hours, neither the peptide H-IFVIDDKSG-OH (SEQ ID NO:50) nor water had an effect on cell morphology (FIG. 3A). The cells treated with either water or H-IFVIDDKSG-OH (SEQ ID NO:50) remained flattened and well-attached to the substratum. In contrast, the cells treated with N-Ac-IFVIDDKSG-NH$_2$ (SEQ ID NO:50) rounded up from each other and were not well-attached to the substratum (FIGS. 3A and 3B; arrows indicate rounded cells). These results demonstrate that the peptide N-Ac-IFVIDDKSG-NH$_2$ (SEQ ID NO:50) interferes with cell adhesion. The amino acid sequence of this peptide is identical to that which is found in the first extracellular domain of OB-cadherin.

Example 3

Detection of OB-cadherin in Metastatic Ovarian Tumor Cells

This Example illustrates the association between OB-cadherin expression and metastasis in ovarian carcinoma cells.

An RT-PCR approach was employed to assay the presence of OB-cadherin mRNA transcripts in two ovarian cancer cell lines: SKOV3 (a metastatic cell line) and OVCAR3 (a noninvasive cell line). The cDNA was synthesized from 1 μg of total RNA by M-MLV Reverse Transcriptase (Gibco/BRL, Burlington, ON) using random hexamers as primers. PCR was performed using the contents of the first-strand reaction and the OB-cadherin-specific primers and Taq polymerase (Boehringer Mannheim, Laval, Que., Canada). The OB-cadherin-specific primers used were:

```
Forward 5'-ACCAGATGTCTGTATCAGA3'     (SEQ ID NO:
                                      33); and Reverse 5'-GTCTCCTGGTCATCATCTGCA-3'  (SEQ ID NO:
                                      34)
```

(Munro and Blaschuk, *Biol. Reprod.* 55:822–827, 1996). To confirm the quality of the RNA used, PCR was also performed using primers for the housekeeping gene, hypoxanthine phosphoribosyltransferase (HPRT). The HPRT-specific primers used were:

Forward 5'-CCTGCTGGATTACATTAAAGCACTG-3' (SEQ ID NO:35); and

Reverse 5'-GTCAAGGGCATATCCAACAACAAAC-3' (SEQ ID NO:36)

(Melton et al., *Proc. Natl. Acad. Sci. USA* 81:2147–2151, 1984). The cycling program was as follows: denaturation at 95° C. for 30 sec.; annealing at 58–60° C. for 45 sec.; polymerization at 72° C. for 1 min.; repeat for 30 cycles. All PCR reactions were performed in parallel with reactions containing no cDNA as a control for contamination of PCR reagents. Products were identified by agarose gel electrophoresis stained with ethidium bromide (Sambrook et al., *Molecular Cloning: A Laboratory Manual*, Cold Spring Harbor Laboratories, Cold Spring Harbor, N.Y., 1989).

The results are presented in FIG. 4, which shows RT-PCR products from SKOV3 (lane 1) and OVCAR3 (lane 2). The primers used are specific for OB-cadherin (OB-cad) and hypoxanthine phosphoribosyltransferase (HPRT) as indicated, with an expected PCR product of 745 bp and 352 bp, respectively. Products were stained with ethidium bromide and resolved by agarose gel electrophoresis, and were all of the expected size. The results indicate that OB-cadherin is expressed by metastatic human ovarian cancer cells, and is not expressed by non-invasive human ovarian cancer cells.

Example 4

Detection of OB-cadherin in Leukemic Cells

This Example illustrates the expression of OB-cadherin in lymphocytes of leukemia patients.

The RT-PCR approach described in Example 3 was employed to assay the presence of OB-cadherin mRNA transcripts in lymphocytes prepared from patients with B-cell chronic lymphocytic leukemia (B-CLL). RT-PCR products (shown in FIG. 5) were generated from lymphocytes of a human B-CLL patient (lane 1) and mouse liver (lane 2). The primers used were specific for OB-cadherin (OB-cad, top panel) and hypoxanthine phosphoribosyltransferase (HPRT, bottom panel), with an expected PCR product of 745 bp and 352 bp, respectively. Products were stained with ethidium bromide and resolved by agarose gel electrophoresis, and were all of the expected size. The results indicate that lymphocytes of a leukemia patient express OB-cadherin.

Using the same approach, RT-PCR products (shown in FIG. 6) were generated from peripheral blood lymphocytes from a normal human (lanes 1 and 3) and a human B-CLL patient (lanes 2 and 4). The primers used were specific for OB-cadherin (lanes 1 and 2) and hypoxanthine phosphoribosyltransferase (HPRT; lanes 3 and 4), with an expected PCR product of 745 bp and 352 bp, respectively. Products were stained with ethidium bromide and resolved by agarose gel electrophoresis, and were all of the expected size. The results indicate that lymphocytes of a leukemia patient, but not a normal patient, express OB-cadherin.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for inhibiting metastasis of OB-cadherin expressing cancer cells, comprising administering to a patient an antimetastatic agent that comprises VIDDK (SEQ ID NO:39) and inhibits OB-cadherin mediated cell adhesion.

2. A method according to claim 1, wherein the agent is a peptide consisting of 5–50 amino acid residues linked by peptide bonds.

3. A method according to claim 1, wherein the agent is a peptide consisting of 5–16 amino acid residues linked by peptide bonds.

4. A method according to claim 2, wherein the agent comprises one or more OB-cadherin CAR sequences selected from the group consisting VIDDK (SEQ ID NO:39), VIDDKS (SEQ ID NO:41), VIDDKSG (SEQ ID NO:44), FVIDDK (SEQ ID NO:45), FVIDDKS (SEQ ID NO:46), FVIDDKSG (SEQ ID NO:47), IFVIDDK (SEQ ID NO:48), IFVIDDKS (SEQ ID NO:49), and IFVIDDKSG (SEQ ID NO:50).

5. A method according to claim 4, wherein the agent comprises a linear peptide having the sequence N-Ac-IFVIDDKSG-NH$_2$ (SEQ ID NO:50).

6. A method according to claim 1, wherein VIDDK (SEQ ID NO:1) is present within a cyclic peptide.

7. A method according to claim 6, wherein the cyclic peptide has the formula:

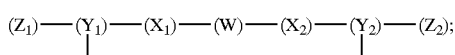

wherein W is a tripeptide DDK;
wherein $X_1$ comprises VI at its carboxyl terminus, and $X_2$ are optional, and if present, are independently selected from the group consisting of amino acid residues and combinations thereof in which the residues are linked by peptide bonds, and wherein $X_1$ and $X_2$ independently range in size from 2 to 10 residues, such that the sum of residues contained within $X_1$ and $X_2$ ranges from 2 to 12;
wherein $Y_1$ and $Y_2$ are independently selected from the group consisting of amino acid residues, and wherein a covalent bond is formed between residues $Y_1$ and $Y_2$; and
wherein $Z_1$ and $Z_2$ are optional, and if present, are independently selected from the group consisting of amino acid residues and combinations thereof in which the residues are linked by peptide bonds.

8. A method according to claim 7, wherein the agent has a sequence selected from the group consisting of:
CVIDDKC (SEQ ID NO:82), CVIDDKSC (SEQ ID NO:84), CVIDDKSGC (SEQ ID NO:87), CFVIDDKC (SEQ ID NO:88), CFVIDDKSC (SEQ ID NO:89), CFVIDDKSGC (SEQ ID NO:90), CIFVIDDKC (SEQ ID NO:91), CIFVIDDKSC (SEQ ID NO:92), CIFVIDDKSGC (SEQ ID NO:93), DVIDDKK (SEQ ID NO:96), DFVIDDKK (SEQ ID NO:97), DIFVIDDKK (SEQ ID NO:98), EVIDDKK (SEQ ID NO:101), EFVIDDKK (SEQ ID NO:102), EIFVIDDKK (SEQ ID NO:103), FVIDDK (SEQ ID NO:104), FVIDDKS (SEQ ID NO:105), FVIDDKSG (SEQ ID NO:106), KVIDDKD (SEQ ID NO:110), KVIDDKSD (SEQ ID NO:112), KVIDDKSGD (SEQ ID NO:115), KFVIDDKD (SEQ ID NO:116), KFVIDDKSD (SEQ ID NO:117), KFVIDDKSGD (SEQ ID NO:118), KIFVIDDKD (SEQ ID NO:119), KIFVIDDKSD (SEQ ID NO:120), KIFVIDDKSGD (SEQ ID NO:121), VIDDK (SEQ ID NO:122), VIDDKS (SEQ ID NO:124), VIDDKSG (SEQ ID NO:125), IFVIDDK (SEQ ID NO:128), IFVIDDKS (SEQ ID NO:129), IFVIDDKSG (SEQ ID NO:130), KVIDDKE (SEQ ID NO:134), KVIDDKSE (SEQ ID NO:136), KVIDDKSGE (SEQ ID NO:139), KFVIDDKE (SEQ ID NO:140), KFVIDDKSE (SEQ ID NO:141), and KFVIDDKSGE (SEQ ID NO:142), KIFVIDDKE (SEQ ID NO:143), KIFVIDDKSE (SEQ ID NO:144), and KIFVIDDKSGE (SEQ ID NO:145).

9. A method according to claim 1, wherein the agent is linked to a drug.

10. A method according to claim 1, wherein the agent is linked to a targeting moiety.

11. A method according to claim 1, wherein the agent is linked to:
(a) a CAR sequence that is specifically recognized by an adhesion molecule selected from the group consisting of cadherins, integrins, occludin, claudins and members of the immunoglobulin superfamily; and/or
(b) an antibody or antigen-binding fragment thereof that specifically binds to a CAR sequence that is specifically recognized by an adhesion molecule selected from the group consisting of cadherins, integrins, occludin, claudins and members of the immunoglobulin superfamily.

12. A method according to claim 1, wherein the agent is present within a pharmaceutical composition comprising a physiologically acceptable carrier.

13. A method according to claim 12, wherein the composition further comprises a drug.

14. A method according to claim 12, wherein the composition further comprises a modulator of cell adhesion comprising:
(a) a CAR sequence that is specifically recognized by an adhesion molecule selected from the group consisting of cadherins, integrins, occludin, claudins and members of the immunoglobulin superfamily; and/or
(b) an antibody or antigen-binding fragment thereof that specifically binds to a CAR sequence that is specifically recognized by an adhesion molecule selected from the group consisting of cadherins, integrins, occludin, claudins and members of the immunoglobulin superfamily.

* * * * *

SEQUENCE LISTING

<160> NUMBER OF SEQ ID NOS: 319

<210> SEQ ID NO 1
<211> LENGTH: 106
<212> TYPE: PRT
<213> ORGANISM: Homo sapien

<400> SEQUENCE: 1

```
Gly Trp Val Trp Asn Gln Phe Phe Val Ile Glu Glu Tyr Thr Gly Pro
 1               5                  10                  15
Asp Pro Val Leu Val Gly Arg Leu His Ser Asp Ile Asp Ser Gly Asp
            20                  25                  30
Gly Asn Ile Lys Tyr Ile Leu Ser Gly Glu Gly Ala Gly Thr Ile Phe
        35                  40                  45
Val Ile Asp Asp Lys Ser Gly Asn Ile His Ala Thr Lys Thr Leu Asp
    50                  55                  60
Arg Glu Glu Arg Ala Gln Tyr Thr Leu Met Ala Gln Ala Val Asp Arg
65                  70                  75                  80
Asp Thr Asn Arg Pro Leu Glu Pro Pro Ser Glu Phe Ile Val Lys Val
                85                  90                  95
Gln Asp Ile Asn Asp Asn Pro Pro Glu Phe
            100                 105
```

<210> SEQ ID NO 2
<211> LENGTH: 106
<212> TYPE: PRT
<213> ORGANISM: Mus musculus

<400> SEQUENCE: 2

```
            Gly Trp Val Trp Asn Gln Phe Phe Val Ile Glu Glu Tyr Thr Gly Pro
            1               5                   10                  15
            Asp Pro Val Leu Val Gly Arg Leu His Ser Asp Ile Asp Ser Gly Asp
                        20                  25                  30
            Gly Asn Ile Lys Tyr Ile Leu Ser Gly Glu Gly Ala Gly Thr Ile Phe
                        35                  40                  45
            Val Ile Asp Asp Lys Ser Gly Asn Ile His Ala Thr Lys Thr Leu Asp
                    50                  55                  60
            Arg Glu Glu Arg Ala Gln Tyr Thr Leu Met Ala Gln Ala Val Asp Arg
            65                  70                  75                  80
            Asp Thr Asn Arg Pro Leu Glu Pro Ser Glu Phe Ile Val Lys Val
                            85                  90                  95
            Gln Asp Ile Asn Asp Asn Pro Pro Glu Phe
                            100                 105
```

<210> SEQ ID NO 3
<211> LENGTH: 106
<212> TYPE: PRT
<213> ORGANISM: Gallus gallus

<400> SEQUENCE: 3

```
            Gly Trp Val Trp Asn Gln Phe Phe Val Ile Glu Glu Tyr Thr Gly Pro
            1               5                   10                  15
            Asp Pro Val Leu Val Gly Arg Leu His Ser Asp Ile Asp Ser Gly Asp
                        20                  25                  30
            Gly Asn Ile Lys Tyr Ile Leu Ser Gly Glu Gly Ala Gly Ile Ile Phe
                        35                  40                  45
            Val Ile Asp Asp Lys Ser Gly Asn Ile His Ala Thr Lys Thr Leu Asp
                    50                  55                  60
            Arg Glu Glu Arg Ala Gln Tyr Thr Leu Thr Ala Gln Ala Val Asp Arg
            65                  70                  75                  80
            Asn Thr Asn Arg Pro Leu Glu Pro Ser Glu Phe Ile Val Lys Val
                            85                  90                  95
            Gln Asp Ile Asn Asp Asn Pro Pro Glu Phe
                            100                 105
```

<210> SEQ ID NO 4
<211> LENGTH: 4
<212> TYPE: PRT
<213> ORGANISM: Unknown
<220> FEATURE:
<223> OTHER INFORMATION: Calcium binding motif of cadherin repeat sequence
<221> NAME/KEY: VARIANT
<222> LOCATION: (1)...(4)
<223> OTHER INFORMATION: Xaa = Any Amino Acid

<400> SEQUENCE: 4

```
      Xaa Asp Xaa Glu
        1
```

<210> SEQ ID NO 5
<211> LENGTH: 5
<212> TYPE: PRT
<213> ORGANISM: Calcium binding motif of cadherin repeat sequencUn
<220> FEATURE:
<223> OTHER INFORMATION: Calcium binding motif of cadherin repeat sequence
<221> NAME/KEY: VARIANT
<222> LOCATION: (1)...(5)
<223> OTHER INFORMATION: Xaa = Any Amino Acid

<400> SEQUENCE: 5

```
      Asp Xaa Xaa Asp Xaa
        1               5
```

<210> SEQ ID NO 6
<211> LENGTH: 4
<212> TYPE: PRT
<213> ORGANISM: Unknown
<220> FEATURE:
<223> OTHER INFORMATION: Calcium binding motif of cadherin repeat sequence

```
<400> SEQUENCE: 6

Leu Asp Arg Glu
        1

<210> SEQ ID NO 7
<211> LENGTH: 4
<212> TYPE: PRT
<213> ORGANISM: Unknown
<220> FEATURE:
<223> OTHER INFORMATION: Calcium binding motif of cadherin repeat sequence

<400> SEQUENCE: 7

Met Asp Arg Glu
        1

<210> SEQ ID NO 8
<211> LENGTH: 4
<212> TYPE: PRT
<213> ORGANISM: Unknown
<220> FEATURE:
<223> OTHER INFORMATION: Calcium binding motif of cadherin repeat sequence

<400> SEQUENCE: 8

Leu Asp Phe Glu
        1

<210> SEQ ID NO 9
<211> LENGTH: 4
<212> TYPE: PRT
<213> ORGANISM: Unknown
<220> FEATURE:
<223> OTHER INFORMATION: Calcium binding motif of cadherin repeat sequence

<400> SEQUENCE: 9

Leu Asp Tyr Glu
        1

<210> SEQ ID NO 10
<211> LENGTH: 4
<212> TYPE: PRT
<213> ORGANISM: Unknown
<220> FEATURE:
<223> OTHER INFORMATION: Calcium binding motif of cadherin repeat sequence

<400> SEQUENCE: 10

Ile Asp Arg Glu
        1

<210> SEQ ID NO 11
<211> LENGTH: 4
<212> TYPE: PRT
<213> ORGANISM: unknown
<220> FEATURE:
<223> OTHER INFORMATION: Calcium binding motif of cadherin repeat sequence

<400> SEQUENCE: 11

Val Asp Arg Glu
        1

<210> SEQ ID NO 12
<211> LENGTH: 4
<212> TYPE: PRT
<213> ORGANISM: Unknown
<220> FEATURE:
<223> OTHER INFORMATION: Calcium binding motif of cadherin repeat sequence

<400> SEQUENCE: 12
```

```
        Ile Asp Phe Glu
          1

<210> SEQ ID NO 13
<211> LENGTH: 11
<212> TYPE: PRT
<213> ORGANISM: Unknown
<220> FEATURE:
<223> OTHER INFORMATION: Calcium binding motif of cadherin repeat sequence
<221> NAME/KEY: VARIANT
<222> LOCATION: (1)...(1)
<223> OTHER INFORMATION: Xaa is either Leucine, Isoleucine or Valine
<221> NAME/KEY: VARIANT
<222> LOCATION: (2)...(2)
<223> OTHER INFORMATION: Xaa = Any Amino Acid
<221> NAME/KEY: VARIANT
<222> LOCATION: (3)...(3)
<223> OTHER INFORMATION: Xaa is either Leucine, Isoleucine or Valine
<221> NAME/KEY: VARIANT
<222> LOCATION: (4)...(4)
<223> OTHER INFORMATION: Xaa = Any Amino Acid
<221> NAME/KEY: VARIANT
<222> LOCATION: (6)...(6)
<223> OTHER INFORMATION: Xaa = Any Amino Acid
<221> NAME/KEY: VARIANT
<222> LOCATION: (9)...(9)
<223> OTHER INFORMATION: Xaa is Asparigine or Histidine
<221> NAME/KEY: VARIANT
<222> LOCATION: (10)...(10)
<223> OTHER INFORMATION: Xaa = Any Amino Acid

<400> SEQUENCE: 13

Xaa Xaa Xaa Xaa Asp Xaa Asn Asp Xaa Xaa Pro
         1               5                  10

<210> SEQ ID NO 14
<211> LENGTH: 5
<212> TYPE: PRT
<213> ORGANISM: Unknown
<220> FEATURE:
<223> OTHER INFORMATION: Calcium binding motif of cadherin repeat sequence
<221> NAME/KEY: VARIANT
<222> LOCATION: (1)...(5)
<223> OTHER INFORMATION: Xaa = Any Amino Acid

<400> SEQUENCE: 14

Asp Xaa Asn Asp Asn
         1               5

<210> SEQ ID NO 15
<211> LENGTH: 9
<212> TYPE: PRT
<213> ORGANISM: Unknown
<220> FEATURE:
<223> OTHER INFORMATION: Consensus OB-cadherin cell adhesion recognition
      sequence including human, mouse and chicken
<221> NAME/KEY: VARIANT
<222> LOCATION: (1)...(1)
<223> OTHER INFORMATION: Xaa = Any Amino Acid
<221> NAME/KEY: VARIANT
<222> LOCATION: (3)...(3)
<223> OTHER INFORMATION: Xaa = Any Amino Acid
<221> NAME/KEY: VARIANT
<222> LOCATION: (4)...(4)
<223> OTHER INFORMATION: Xaa is Leucine, Isoleucine or Valine
<221> NAME/KEY: VARIANT
<222> LOCATION: (5)...(5)
<223> OTHER INFORMATION: Xaa is Aspartic Acid, Asparagine or Glutamic Acid
<221> NAME/KEY: VARIANT
<222> LOCATION: (6)...(7)
<223> OTHER INFORMATION: Xaa = Any Amino Acid
<221> NAME/KEY: VARIANT
<222> LOCATION: (8)...(8)
```

```
<223> OTHER INFORMATION: Xaa is Serine, Threonine or Asparagine

<400> SEQUENCE: 15

Xaa Phe Xaa Xaa Xaa Xaa Xaa Xaa Gly
        1               5

<210> SEQ ID NO 16
<211> LENGTH: 5
<212> TYPE: PRT
<213> ORGANISM: Unknown
<220> FEATURE:
<223> OTHER INFORMATION: Cadherin cell adhesion recognition sequence bound
      by alpha-6-beta-1 integrin

<400> SEQUENCE: 16

Tyr Ile Gly Ser Arg
         1               5

<210> SEQ ID NO 17
<211> LENGTH: 10
<212> TYPE: PRT
<213> ORGANISM: Unknown
<220> FEATURE:
<223> OTHER INFORMATION: N-CAM cell adhesion recognition sequence

<400> SEQUENCE: 17

Lys Tyr Ser Phe Asn Tyr Asp Gly Ser Glu
         1               5                  10

<210> SEQ ID NO 18
<211> LENGTH: 4
<212> TYPE: PRT
<213> ORGANISM: Unknown
<220> FEATURE:
<223> OTHER INFORMATION: Occludin cell adhesion recognition sequence

<400> SEQUENCE: 18

Leu Tyr His Tyr
          1

<210> SEQ ID NO 19
<211> LENGTH: 4
<212> TYPE: PRT
<213> ORGANISM: Unknown
<220> FEATURE:
<223> OTHER INFORMATION: Claudin cell adhesion recognition sequence

<400> SEQUENCE: 19

Ile Tyr Ser Tyr
          1

<210> SEQ ID NO 20
<211> LENGTH: 4
<212> TYPE: PRT
<213> ORGANISM: Unknown
<220> FEATURE:
<223> OTHER INFORMATION: Claudin cell adhesion recognition sequence

<400> SEQUENCE: 20

Thr Ser Ser Tyr
          1

<210> SEQ ID NO 21
<211> LENGTH: 4
<212> TYPE: PRT
<213> ORGANISM: Unknown
<220> FEATURE:
```

```
<223> OTHER INFORMATION: Claudin cell adhesion recognition sequence

<400> SEQUENCE: 21

Val Thr Ala Phe
        1

<210> SEQ ID NO 22
<211> LENGTH: 4
<212> TYPE: PRT
<213> ORGANISM: Unknown
<220> FEATURE:
<223> OTHER INFORMATION: Claudin cell adhesion recognition sequence

<400> SEQUENCE: 22

Val Ser Ala Phe
        1

<210> SEQ ID NO 23
<211> LENGTH: 5
<212> TYPE: PRT
<213> ORGANISM: Artificial Sequence
<220> FEATURE:
<223> OTHER INFORMATION: Synthesized Cyclic Peptide that contain an
      OB-cadherin cell adhesion recognition sequence
<221> NAME/KEY: MOD_RES
<222> LOCATION: (5)...(5)
<223> OTHER INFORMATION: Where Xaa is beta,beta dimethyl cysteine

<400> SEQUENCE: 23

Cys Asp Asp Lys Xaa
        1               5

<210> SEQ ID NO 24
<211> LENGTH: 10
<212> TYPE: PRT
<213> ORGANISM: Artificial Sequence
<220> FEATURE:
<223> OTHER INFORMATION: Synthesized Cyclic Peptide with an OB-cadherin
      cell adhesion sequence
<221> NAME/KEY: MOD_RES
<222> LOCATION: (2)...(2)
<223> OTHER INFORMATION: Where Xaa is beta,beta-tetramethylene cysteine

<400> SEQUENCE: 24

Ile Xaa Val Ile Asp Asp Lys Ser Cys Glu
        1               5                  10

<210> SEQ ID NO 25
<211> LENGTH: 10
<212> TYPE: PRT
<213> ORGANISM: Artificial Sequence
<220> FEATURE:
<223> OTHER INFORMATION: Synthesized Cyclic Peptide with an OB-cadherin
      cell adhesion sequence
<221> NAME/KEY: MOD_RES
<222> LOCATION: (2)...(2)
<223> OTHER INFORMATION: Where Xaa is beta,beta pentamethylene cysteine

<400> SEQUENCE: 25

Ile Xaa Val Ile Asp Asp Lys Ser Gly Cys
        1               5                  10

<210> SEQ ID NO 26
<211> LENGTH: 9
<212> TYPE: PRT
<213> ORGANISM: Artificial Sequence
<220> FEATURE:
<223> OTHER INFORMATION: Synthesized Cyclic Peptide with an OB-cadherin
      cell adhesion sequence
```

```
<221> NAME/KEY: MOD_RES
<222> LOCATION: (1)...(1)
<223> OTHER INFORMATION: Where Xaa is beta-mercaptopropionic acid

<400> SEQUENCE: 26

Xaa Val Ile Asp Asp Lys Ser Gly Cys
       1               5

<210> SEQ ID NO 27
<211> LENGTH: 9
<212> TYPE: PRT
<213> ORGANISM: Artificial Sequence
<220> FEATURE:
<223> OTHER INFORMATION: Synthesized Cyclic Peptide with an OB-cadherin
      cell adhesion sequence
<221> NAME/KEY: MOD_RES
<222> LOCATION: (1)...(1)
<223> OTHER INFORMATION: Where Xaa is beta,beta-pentamethylene-beta-
      mercaptopropionic acid

<400> SEQUENCE: 27

Xaa Val Ile Asp Asp Lys Ser Gly Cys
       1               5

<210> SEQ ID NO 28
<211> LENGTH: 5
<212> TYPE: PRT
<213> ORGANISM: Artificial Sequence
<220> FEATURE:
<223> OTHER INFORMATION: Synthesized Cyclic Peptide with an OB-cadherin
      cell adhesion sequence
<221> NAME/KEY: MOD_RES
<222> LOCATION: (4)...(4)
<223> OTHER INFORMATION: Where Ser is D-Serine

<400> SEQUENCE: 28

Asp Asp Lys Ser Ser
       1               5

<210> SEQ ID NO 29
<211> LENGTH: 4
<212> TYPE: PRT
<213> ORGANISM: Artificial Sequence
<220> FEATURE:
<223> OTHER INFORMATION: Synthesized cyclic peptide

<400> SEQUENCE: 29

Trp Gly Gly Trp
       1

<210> SEQ ID NO 30
<211> LENGTH: 6
<212> TYPE: PRT
<213> ORGANISM: Unknown
<220> FEATURE:
<223> OTHER INFORMATION: Classical cell adhesion recognition sequence

<400> SEQUENCE: 30

Ser His Ala Val Ser Ser
       1               5

<210> SEQ ID NO 31
<211> LENGTH: 6
<212> TYPE: PRT
<213> ORGANISM: Unknown
<220> FEATURE:
<223> OTHER INFORMATION: Classical cell adhesion recognition sequence

<400> SEQUENCE: 31
```

```
                Ala His Ala Val Asp Ile
                  1               5

<210> SEQ ID NO 32
<211> LENGTH: 9
<212> TYPE: PRT
<213> ORGANISM: Unknown
<220> FEATURE:
<223> OTHER INFORMATION: A cell adhesion recognition sequence for junction
      associated molecule (JAM)

<400> SEQUENCE: 32

Ser Phe Thr Ile Asp Pro Lys Ser Gly
         1               5

<210> SEQ ID NO 33
<211> LENGTH: 19
<212> TYPE: DNA
<213> ORGANISM: Artificial Sequence
<220> FEATURE:
<223> OTHER INFORMATION: OB-cadherin specific primer

<400> SEQUENCE: 33
accagatgtc tgtatcaga                                       19

<210> SEQ ID NO 34
<211> LENGTH: 21
<212> TYPE: DNA
<213> ORGANISM: Artificial Sequence
<220> FEATURE:
<223> OTHER INFORMATION: OB-cadherin specific primer

<400> SEQUENCE: 34
gtctcctggt catcatctgc a                                    21

<210> SEQ ID NO 35
<211> LENGTH: 25
<212> TYPE: DNA
<213> ORGANISM: Artificial Sequence
<220> FEATURE:
<223> OTHER INFORMATION: Hypoxanthine phosphoribosyltransferase specific
      prime

<400> SEQUENCE: 35
cctgctggat tacattaaag cactg                                25

<210> SEQ ID NO 36
<211> LENGTH: 25
<212> TYPE: DNA
<213> ORGANISM: Artificial Sequence
<220> FEATURE:
<223> OTHER INFORMATION: Hypoxanthine phosphoribosyltransferase specific
      prime

<400> SEQUENCE: 36
gtcaagggca tatccaacaa caaac                                25

<210> SEQ ID NO 37
<211> LENGTH: 4
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 37
```

```
        Ile Asp Asp Lys
        1

<210> SEQ ID NO 38
<211> LENGTH: 4
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 38

Asp Asp Lys Ser
        1

<210> SEQ ID NO 39
<211> LENGTH: 5
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 39

Val Ile Asp Asp Lys
        1               5

<210> SEQ ID NO 40
<211> LENGTH: 5
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 40

Ile Asp Asp Lys Ser
        1               5

<210> SEQ ID NO 41
<211> LENGTH: 6
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 41

Val Ile Asp Asp Lys Ser
        1               5

<210> SEQ ID NO 42
<211> LENGTH: 5
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 42

Asp Asp Lys Ser Gly
        1               5

<210> SEQ ID NO 43
<211> LENGTH: 6
<212> TYPE: PRT
<213> ORGANISM: Artificial Sequence
<220> FEATURE:
```

```
<223> OTHER INFORMATION: Synthesized peptide with an OB-cadherin cell
      adhesion recognition sequence

<400> SEQUENCE: 43

Ile Asp Asp Lys Ser Gly
        1               5

<210> SEQ ID NO 44
<211> LENGTH: 7
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 44

Val Ile Asp Asp Lys Ser Gly
        1               5

<210> SEQ ID NO 45
<211> LENGTH: 6
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 45

Phe Val Ile Asp Asp Lys
        1               5

<210> SEQ ID NO 46
<211> LENGTH: 7
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 46

Phe Val Ile Asp Asp Lys Ser
        1               5

<210> SEQ ID NO 47
<211> LENGTH: 8
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 47

Phe Val Ile Asp Asp Lys Ser Gly
        1               5

<210> SEQ ID NO 48
<211> LENGTH: 7
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 48

Ile Phe Val Ile Asp Asp Lys
        1               5
```

```
<210> SEQ ID NO 49
<211> LENGTH: 8
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 49

Ile Phe Val Ile Asp Asp Lys Ser
        1               5

<210> SEQ ID NO 50
<211> LENGTH: 9
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 50

Ile Phe Val Ile Asp Asp Lys Ser Gly
        1               5

<210> SEQ ID NO 51
<211> LENGTH: 4
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 51

Ile Glu Glu Tyr
        1

<210> SEQ ID NO 52
<211> LENGTH: 4
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 52

Glu Glu Tyr Thr
        1

<210> SEQ ID NO 53
<211> LENGTH: 5
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 53

Val Ile Glu Glu Tyr
        1               5

<210> SEQ ID NO 54
<211> LENGTH: 5
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 54
```

```
        Ile Glu Glu Tyr Thr
        1               5

<210> SEQ ID NO 55
<211> LENGTH: 6
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 55

Val Ile Glu Glu Tyr Thr
        1               5

<210> SEQ ID NO 56
<211> LENGTH: 5
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 56

Glu Glu Tyr Thr Gly
        1               5

<210> SEQ ID NO 57
<211> LENGTH: 6
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 57

Ile Glu Glu Tyr Thr Gly
        1               5

<210> SEQ ID NO 58
<211> LENGTH: 7
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 58

Val Ile Glu Glu Tyr Thr Gly
        1               5

<210> SEQ ID NO 59
<211> LENGTH: 6
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 59

Phe Val Ile Glu Glu Tyr
        1               5

<210> SEQ ID NO 60
<211> LENGTH: 7
<212> TYPE: PRT
<213> ORGANISM: Artificial Sequence
```

```
<220> FEATURE:
<223> OTHER INFORMATION: Synthesized peptide with an OB-cadherin cell
      adhesion recognition sequence

<400> SEQUENCE: 60

Phe Val Ile Glu Glu Tyr Thr
       1               5

<210> SEQ ID NO 61
<211> LENGTH: 8
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 61

Phe Val Ile Glu Glu Tyr Thr Gly
       1               5

<210> SEQ ID NO 62
<211> LENGTH: 7
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 62

Phe Phe Val Ile Glu Glu Tyr
       1               5

<210> SEQ ID NO 63
<211> LENGTH: 8
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 63

Phe Phe Val Ile Glu Glu Tyr Thr
       1               5

<210> SEQ ID NO 64
<211> LENGTH: 9
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 64

Phe Phe Val Ile Glu Glu Tyr Thr Gly
       1               5

<210> SEQ ID NO 65
<211> LENGTH: 4
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 65

Val Glu Ala Gln
       1
```

```
<210> SEQ ID NO 66
<211> LENGTH: 4
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 66

Glu Ala Gln Thr
        1

<210> SEQ ID NO 67
<211> LENGTH: 5
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 67

Ser Val Glu Ala Gln
        1               5

<210> SEQ ID NO 68
<211> LENGTH: 5
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 68

Val Glu Ala Gln Thr
        1               5

<210> SEQ ID NO 69
<211> LENGTH: 6
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 69

Ser Val Glu Ala Gln Thr
        1               5

<210> SEQ ID NO 70
<211> LENGTH: 5
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 70

Glu Ala Gln Thr Gly
        1               5

<210> SEQ ID NO 71
<211> LENGTH: 6
<212> TYPE: PRT
<213> ORGANISM: Artificial Sequence
<220> FEATURE:
<223> OTHER INFORMATION: Synthesized peptide with an OB-cadherin cell
      adhesion recognition sequence
```

-continued

```
<400> SEQUENCE: 71

Val Glu Ala Gln Thr Gly
      1               5

<210> SEQ ID NO 72
<211> LENGTH: 7
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 72

Ser Val Glu Ala Gln Thr Gly
      1               5

<210> SEQ ID NO 73
<211> LENGTH: 6
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 73

Phe Ser Val Glu Ala Gln
      1               5

<210> SEQ ID NO 74
<211> LENGTH: 7
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 74

Phe Ser Val Glu Ala Gln Thr
      1               5

<210> SEQ ID NO 75
<211> LENGTH: 8
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 75

Phe Ser Val Glu Ala Gln Thr Gly
      1               5

<210> SEQ ID NO 76
<211> LENGTH: 7
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 76

Tyr Phe Ser Val Glu Ala Gln
      1               5

<210> SEQ ID NO 77
<211> LENGTH: 8
<212> TYPE: PRT
```

```
<213> ORGANISM: Artificial Sequence
<220> FEATURE:
<223> OTHER INFORMATION: Synthesized peptide with an OB-cadherin cell
      adhesion recognition sequence

<400> SEQUENCE: 77

Tyr Phe Ser Val Glu Ala Gln Thr
       1               5

<210> SEQ ID NO 78
<211> LENGTH: 9
<212> TYPE: PRT
<213> ORGANISM: Artificial Sequence
<220> FEATURE:
<223> OTHER INFORMATION: Synthesized peptide with an OB-cadherin cell
      adhesion recognition sequence

<400> SEQUENCE: 78

Tyr Phe Ser Val Glu Ala Gln Thr Gly
       1               5

<210> SEQ ID NO 79
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 79

Cys Asp Asp Lys Cys
       1               5

<210> SEQ ID NO 80
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 80

Cys Ile Asp Asp Lys Cys
       1               5

<210> SEQ ID NO 81
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 81

Cys Asp Asp Lys Ser Cys
       1               5

<210> SEQ ID NO 82
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 82

Cys Val Ile Asp Asp Lys Cys
       1               5
```

```
<210> SEQ ID NO 83
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 83

Cys Ile Asp Asp Lys Ser Cys
      1               5

<210> SEQ ID NO 84
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 84

Cys Val Ile Asp Asp Lys Ser Cys
      1               5

<210> SEQ ID NO 85
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 85

Cys Asp Asp Lys Ser Gly Cys
      1               5

<210> SEQ ID NO 86
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 86

Cys Ile Asp Asp Lys Ser Gly Cys
      1               5

<210> SEQ ID NO 87
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 87

Cys Val Ile Asp Asp Lys Ser Gly Cys
      1               5

<210> SEQ ID NO 88
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence
```

```
<400> SEQUENCE: 88

Cys Phe Val Ile Asp Asp Lys Cys
       1               5

<210> SEQ ID NO 89
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 89

Cys Phe Val Ile Asp Asp Lys Ser Cys
       1               5

<210> SEQ ID NO 90
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 90

Cys Phe Val Ile Asp Asp Lys Ser Gly Cys
       1               5                  10

<210> SEQ ID NO 91
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 91

Cys Ile Phe Val Ile Asp Asp Lys Cys
       1               5

<210> SEQ ID NO 92
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 92

Cys Ile Phe Val Ile Asp Asp Lys Ser Cys
       1               5                  10

<210> SEQ ID NO 93
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 93

Cys Ile Phe Val Ile Asp Asp Lys Ser Gly Cys
       1               5                  10

<210> SEQ ID NO 94
<211> LENGTH: 5
```

```
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 94

Asp Asp Asp Lys Lys
        1               5

<210> SEQ ID NO 95
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 95

Asp Ile Asp Asp Lys Lys
        1               5

<210> SEQ ID NO 96
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 96

Asp Val Ile Asp Asp Lys Lys
        1               5

<210> SEQ ID NO 97
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 97

Asp Phe Val Ile Asp Asp Lys Lys
        1               5

<210> SEQ ID NO 98
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 98

Asp Ile Phe Val Ile Asp Asp Lys Lys
        1               5

<210> SEQ ID NO 99
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 99

Glu Asp Asp Lys Lys
```

-continued

```
                        1               5

<210> SEQ ID NO 100
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 100

Glu Ile Asp Asp Lys Lys
          1               5

<210> SEQ ID NO 101
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 101

Glu Val Ile Asp Asp Lys Lys
          1               5

<210> SEQ ID NO 102
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 102

Glu Phe Val Ile Asp Asp Lys Lys
          1               5

<210> SEQ ID NO 103
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 103

Glu Ile Phe Val Ile Asp Asp Lys Lys
          1               5

<210> SEQ ID NO 104
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 104

Phe Val Ile Asp Asp Lys
          1               5

<210> SEQ ID NO 105
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
``` cell adhesion recognition sequence

<400> SEQUENCE: 105

Phe Val Ile Asp Asp Lys Ser
       1            5

<210> SEQ ID NO 106
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 106

Phe Val Ile Asp Asp Lys Ser Gly
       1            5

<210> SEQ ID NO 107
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 107

Lys Asp Asp Lys Asp
       1            5

<210> SEQ ID NO 108
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 108

Lys Ile Asp Asp Lys Asp
       1            5

<210> SEQ ID NO 109
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 109

Lys Asp Asp Lys Ser Asp
       1            5

<210> SEQ ID NO 110
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 110

Lys Val Ile Asp Asp Lys Asp
       1            5

<210> SEQ ID NO 111

```
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 111

Lys Ile Asp Asp Lys Ser Asp
       1               5

<210> SEQ ID NO 112
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 112

Lys Val Ile Asp Asp Lys Ser Asp
       1               5

<210> SEQ ID NO 113
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 113

Lys Asp Asp Lys Ser Gly Asp
       1               5

<210> SEQ ID NO 114
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 114

Lys Ile Asp Asp Lys Ser Gly Asp
       1               5

<210> SEQ ID NO 115
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 115

Lys Val Ile Asp Asp Lys Ser Gly Asp
       1               5

<210> SEQ ID NO 116
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 116
```

```
        Lys Phe Val Ile Asp Asp Lys Asp
          1               5

<210> SEQ ID NO 117
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 117

Lys Phe Val Ile Asp Asp Lys Ser Asp
          1               5

<210> SEQ ID NO 118
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 118

Lys Phe Val Ile Asp Asp Lys Ser Gly Asp
          1               5                  10

<210> SEQ ID NO 119
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 119

Lys Ile Phe Val Ile Asp Asp Lys Asp
          1               5

<210> SEQ ID NO 120
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 120

Lys Ile Phe Val Ile Asp Asp Lys Ser Asp
          1               5                  10

<210> SEQ ID NO 121
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 121

Lys Ile Phe Val Ile Asp Asp Lys Ser Gly Asp
          1               5                  10

<210> SEQ ID NO 122
<211> LENGTH: 5
<212> TYPE: PRT
<213> ORGANISM: Artificial Sequence
<220> FEATURE:
```

```
<223> OTHER INFORMATION: Synthesized cyclic peptide with an OB-cadherin
      cell adhesion recognition sequence

<400> SEQUENCE: 122

Val Ile Asp Asp Lys
      1               5

<210> SEQ ID NO 123
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 123

Ile Asp Asp Lys Ser
      1               5

<210> SEQ ID NO 124
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 124

Val Ile Asp Asp Lys Ser
      1               5

<210> SEQ ID NO 125
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 125

Val Ile Asp Asp Lys Ser Gly
      1               5

<210> SEQ ID NO 126
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 126

Asp Asp Lys Ser Gly
      1               5

<210> SEQ ID NO 127
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 127

Ile Asp Asp Lys Ser Gly
      1               5
```

```
<210> SEQ ID NO 128
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 128

Ile Phe Val Ile Asp Asp Lys
      1               5

<210> SEQ ID NO 129
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 129

Ile Phe Val Ile Asp Asp Lys Ser
      1               5

<210> SEQ ID NO 130
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 130

Ile Phe Val Ile Asp Asp Lys Ser Gly
      1               5

<210> SEQ ID NO 131
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 131

Lys Asp Asp Lys Glu
      1               5

<210> SEQ ID NO 132
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 132

Lys Ile Asp Asp Lys Glu
      1               5

<210> SEQ ID NO 133
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 133
```

Lys Asp Asp Lys Ser Glu
            1               5

<210> SEQ ID NO 134
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 134

Lys Val Ile Asp Asp Lys Glu
            1               5

<210> SEQ ID NO 135
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 135

Lys Ile Asp Asp Lys Ser Glu
            1               5

<210> SEQ ID NO 136
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 136

Lys Val Ile Asp Asp Lys Ser Glu
            1               5

<210> SEQ ID NO 137
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 137

Lys Asp Asp Lys Ser Gly Glu
            1               5

<210> SEQ ID NO 138
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 138

Lys Ile Asp Asp Lys Ser Gly Glu
            1               5

<210> SEQ ID NO 139
<211> LENGTH: 9
<212> TYPE: PRT
<213> ORGANISM: Artificial Sequence

```
<220> FEATURE:
<223> OTHER INFORMATION: Synthesized cyclic peptide with an OB-cadherin
      cell adhesion recognition sequence

<400> SEQUENCE: 139

Lys Val Ile Asp Asp Lys Ser Gly Glu
      1               5

<210> SEQ ID NO 140
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 140

Lys Phe Val Ile Asp Asp Lys Glu
      1               5

<210> SEQ ID NO 141
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 141

Lys Phe Val Ile Asp Asp Lys Ser Glu
      1               5

<210> SEQ ID NO 142
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 142

Lys Phe Val Ile Asp Asp Lys Ser Gly Glu
      1               5                   10

<210> SEQ ID NO 143
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 143

Lys Ile Phe Val Ile Asp Asp Lys Glu
      1               5

<210> SEQ ID NO 144
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 144

Lys Ile Phe Val Ile Asp Asp Lys Ser Glu
      1               5                   10
```

```
<210> SEQ ID NO 145
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 145

Lys Ile Phe Val Ile Asp Asp Lys Ser Gly Glu
       1               5                  10

<210> SEQ ID NO 146
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 146

Cys Glu Glu Tyr Cys
       1               5

<210> SEQ ID NO 147
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 147

Cys Ile Glu Glu Tyr Cys
       1               5

<210> SEQ ID NO 148
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 148

Cys Glu Glu Tyr Thr Cys
       1               5

<210> SEQ ID NO 149
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 149

Cys Val Ile Glu Glu Tyr Cys
       1               5

<210> SEQ ID NO 150
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence
```

```
<400> SEQUENCE: 150

Cys Ile Glu Glu Tyr Thr Cys
      1               5

<210> SEQ ID NO 151
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 151

Cys Val Ile Glu Glu Tyr Thr Cys
      1               5

<210> SEQ ID NO 152
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 152

Cys Glu Glu Tyr Thr Gly Cys
      1               5

<210> SEQ ID NO 153
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 153

Cys Ile Glu Glu Tyr Thr Gly Cys
      1               5

<210> SEQ ID NO 154
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 154

Cys Val Ile Glu Glu Tyr Thr Gly Cys
      1               5

<210> SEQ ID NO 155
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 155

Cys Phe Val Ile Glu Glu Tyr Cys
      1               5

<210> SEQ ID NO 156
<211> LENGTH: 9
<212> TYPE: PRT
```

```
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 156

Cys Phe Val Ile Glu Glu Tyr Thr Cys
       1               5

<210> SEQ ID NO 157
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 157

Cys Phe Val Ile Glu Glu Tyr Thr Gly Cys
       1               5                  10

<210> SEQ ID NO 158
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 158

Cys Phe Phe Val Ile Glu Glu Tyr Cys
       1               5

<210> SEQ ID NO 159
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 159

Cys Phe Phe Val Ile Glu Glu Tyr Thr Cys
       1               5                  10

<210> SEQ ID NO 160
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 160

Cys Phe Phe Val Ile Glu Glu Tyr Thr Gly Cys
       1               5                  10

<210> SEQ ID NO 161
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 161

Lys Glu Glu Tyr Asp
       1               5
```

<210> SEQ ID NO 162
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 162

Lys Ile Glu Glu Tyr Asp
    1               5

<210> SEQ ID NO 163
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 163

Lys Glu Glu Tyr Thr Asp
    1               5

<210> SEQ ID NO 164
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 164

Lys Val Ile Glu Glu Tyr Asp
    1               5

<210> SEQ ID NO 165
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 165

Lys Ile Glu Glu Tyr Thr Asp
    1               5

<210> SEQ ID NO 166
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 166

Lys Val Ile Glu Glu Tyr Thr Asp
    1               5

<210> SEQ ID NO 167
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

```
<400> SEQUENCE: 167

Lys Glu Glu Tyr Thr Gly Cys Asp
      1               5

<210> SEQ ID NO 168
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 168

Lys Ile Glu Glu Tyr Thr Gly Asp
      1               5

<210> SEQ ID NO 169
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 169

Lys Val Ile Glu Glu Tyr Thr Gly Asp
      1               5

<210> SEQ ID NO 170
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 170

Lys Phe Val Ile Glu Glu Tyr Asp
      1               5

<210> SEQ ID NO 171
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 171

Lys Phe Val Ile Glu Glu Tyr Thr Asp
      1               5

<210> SEQ ID NO 172
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 172

Lys Phe Val Ile Glu Glu Tyr Thr Gly Asp
      1               5                   10

<210> SEQ ID NO 173
<211> LENGTH: 9
```

```
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 173

Lys Phe Phe Val Ile Glu Glu Tyr Asp
        1               5

<210> SEQ ID NO 174
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 174

Lys Phe Phe Val Ile Glu Glu Tyr Thr Asp
        1               5                  10

<210> SEQ ID NO 175
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 175

Lys Phe Phe Val Ile Glu Glu Tyr Thr Gly Asp
        1               5                  10

<210> SEQ ID NO 176
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 176

Glu Glu Glu Tyr Lys
        1               5

<210> SEQ ID NO 177
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 177

Glu Ile Glu Glu Tyr Lys
        1               5

<210> SEQ ID NO 178
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 178

Glu Glu Glu Tyr Thr Lys
```

```
          1               5

<210> SEQ ID NO 179
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 179

Glu Val Ile Glu Glu Tyr Lys
       1               5

<210> SEQ ID NO 180
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 180

Glu Ile Glu Glu Tyr Thr Lys
       1               5

<210> SEQ ID NO 181
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 181

Glu Val Ile Glu Glu Tyr Thr Lys
       1               5

<210> SEQ ID NO 182
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 182

Glu Glu Glu Tyr Thr Gly Lys
       1               5

<210> SEQ ID NO 183
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 183

Glu Ile Glu Glu Tyr Thr Gly Lys
       1               5

<210> SEQ ID NO 184
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
``` cell adhesion recognition sequence

<400> SEQUENCE: 184

Glu Val Ile Glu Glu Tyr Thr Gly Lys
       1             5

<210> SEQ ID NO 185
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 185

Glu Phe Val Ile Glu Glu Tyr Lys
       1             5

<210> SEQ ID NO 186
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 186

Glu Phe Val Ile Glu Glu Tyr Thr Lys
       1             5

<210> SEQ ID NO 187
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 187

Glu Phe Val Ile Glu Glu Tyr Thr Gly Lys
       1             5             10

<210> SEQ ID NO 188
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 188

Glu Phe Phe Val Ile Glu Glu Tyr Lys
       1             5

<210> SEQ ID NO 189
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 189

Glu Phe Phe Val Ile Glu Glu Tyr Thr Lys
       1             5             10

<210> SEQ ID NO 190

```
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 190

Glu Phe Phe Val Ile Glu Glu Tyr Thr Gly Lys
     1               5                   10

<210> SEQ ID NO 191
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 191

Asp Cys Glu Glu Tyr Lys
     1               5

<210> SEQ ID NO 192
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 192

Asp Ile Glu Glu Tyr Cys Lys
     1               5

<210> SEQ ID NO 193
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 193

Asp Glu Glu Tyr Thr Lys
     1               5

<210> SEQ ID NO 194
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 194

Asp Val Ile Glu Glu Tyr Lys
     1               5

<210> SEQ ID NO 195
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 195
```

```
            Asp Ile Glu Glu Tyr Thr Lys
              1               5

<210> SEQ ID NO 196
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 196

Asp Val Ile Glu Glu Tyr Thr Lys
            1               5

<210> SEQ ID NO 197
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 197

Asp Glu Glu Tyr Thr Gly Lys
            1               5

<210> SEQ ID NO 198
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 198

Asp Ile Glu Glu Tyr Thr Gly Lys
            1               5

<210> SEQ ID NO 199
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 199

Asp Val Ile Glu Glu Tyr Thr Gly Lys
            1               5

<210> SEQ ID NO 200
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 200

Asp Phe Val Ile Glu Glu Tyr Lys
            1               5

<210> SEQ ID NO 201
<211> LENGTH: 9
<212> TYPE: PRT
<213> ORGANISM: Artificial Sequence
<220> FEATURE:
```

```
<223> OTHER INFORMATION: Synthesized cyclic peptide with an OB-cadherin
      cell adhesion recognition sequence

<400> SEQUENCE: 201

Asp Phe Val Ile Glu Glu Tyr Thr Lys
      1               5

<210> SEQ ID NO 202
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 202

Asp Phe Val Ile Glu Glu Tyr Thr Gly Lys
      1               5                   10

<210> SEQ ID NO 203
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 203

Asp Phe Phe Val Ile Glu Glu Tyr Lys
      1               5

<210> SEQ ID NO 204
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 204

Asp Phe Phe Val Ile Glu Glu Tyr Thr Lys
      1               5                   10

<210> SEQ ID NO 205
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 205

Asp Phe Phe Val Ile Glu Glu Tyr Thr Gly Lys
      1               5                   10

<210> SEQ ID NO 206
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 206

Lys Glu Glu Tyr Glu
      1               5
```

```
<210> SEQ ID NO 207
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 207

Lys Ile Glu Glu Tyr Glu
      1               5

<210> SEQ ID NO 208
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 208

Lys Glu Glu Tyr Thr Glu
      1               5

<210> SEQ ID NO 209
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 209

Lys Val Ile Glu Glu Tyr Glu
      1               5

<210> SEQ ID NO 210
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 210

Lys Ile Glu Glu Tyr Thr Glu
      1               5

<210> SEQ ID NO 211
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 211

Lys Val Ile Glu Glu Tyr Thr Glu
      1               5

<210> SEQ ID NO 212
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 212
```

```
        Lys Glu Glu Tyr Thr Gly Glu
          1               5
```

<210> SEQ ID NO 213
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 213

```
        Lys Ile Glu Glu Tyr Thr Gly Glu
          1               5
```

<210> SEQ ID NO 214
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 214

```
        Lys Val Ile Glu Glu Tyr Thr Gly Glu
          1               5
```

<210> SEQ ID NO 215
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 215

```
        Lys Phe Val Ile Glu Glu Tyr Glu
          1               5
```

<210> SEQ ID NO 216
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 216

```
        Lys Phe Val Ile Glu Glu Tyr Thr Glu
          1               5
```

<210> SEQ ID NO 217
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 217

```
        Lys Phe Val Ile Glu Glu Tyr Thr Gly Glu
          1               5                  10
```

<210> SEQ ID NO 218
<211> LENGTH: 9
<212> TYPE: PRT
<213> ORGANISM: Artificial Sequence

```
<220> FEATURE:
<223> OTHER INFORMATION: Synthesized cyclic peptide with an OB-cadherin
      cell adhesion recognition sequence

<400> SEQUENCE: 218

Lys Phe Phe Val Ile Glu Glu Tyr Glu
      1               5

<210> SEQ ID NO 219
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 219

Lys Phe Phe Val Ile Glu Glu Tyr Thr Glu
      1               5                   10

<210> SEQ ID NO 220
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 220

Lys Phe Phe Val Ile Glu Glu Tyr Thr Gly Glu
      1               5                   10

<210> SEQ ID NO 221
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 221

Val Ile Glu Glu Tyr
      1               5

<210> SEQ ID NO 222
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 222

Ile Glu Glu Tyr Thr
      1               5

<210> SEQ ID NO 223
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 223

Val Ile Glu Glu Tyr Thr
      1               5
```

```
<210> SEQ ID NO 224
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 224

Glu Glu Tyr Thr Gly
      1               5

<210> SEQ ID NO 225
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 225

Ile Glu Glu Tyr Thr Gly
      1               5

<210> SEQ ID NO 226
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 226

Val Ile Glu Glu Tyr Thr Gly
      1               5

<210> SEQ ID NO 227
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 227

Phe Val Ile Glu Glu Tyr
      1               5

<210> SEQ ID NO 228
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 228

Phe Val Ile Glu Glu Tyr Thr
      1               5

<210> SEQ ID NO 229
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence
```

-continued

```
<400> SEQUENCE: 229

Phe Val Ile Glu Glu Tyr Thr Gly
      1               5

<210> SEQ ID NO 230
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 230

Phe Phe Val Ile Glu Glu Tyr
      1               5

<210> SEQ ID NO 231
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 231

Phe Phe Val Ile Glu Glu Tyr Thr
      1               5

<210> SEQ ID NO 232
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 232

Phe Phe Val Ile Glu Glu Tyr Thr Gly
      1               5

<210> SEQ ID NO 233
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 233

Cys Glu Ala Gln Cys
      1               5

<210> SEQ ID NO 234
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 234

Cys Val Glu Ala Gln Cys
      1               5

<210> SEQ ID NO 235
<211> LENGTH: 6
<212> TYPE: PRT
```

```
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 235

Cys Glu Ala Gln Thr Cys
        1               5

<210> SEQ ID NO 236
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 236

Cys Ser Val Glu Ala Gln Cys
        1               5

<210> SEQ ID NO 237
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 237

Cys Val Glu Ala Gln Thr Cys
        1               5

<210> SEQ ID NO 238
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 238

Cys Ser Val Glu Ala Gln Thr Cys
        1               5

<210> SEQ ID NO 239
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 239

Cys Glu Ala Gln Thr Gly Cys
        1               5

<210> SEQ ID NO 240
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 240

Cys Val Glu Ala Gln Thr Gly Cys
        1               5
```

<210> SEQ ID NO 241
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 241

Cys Ser Val Glu Ala Gln Thr Gly Cys
    1               5

<210> SEQ ID NO 242
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 242

Cys Phe Ser Val Glu Ala Gln Cys
    1               5

<210> SEQ ID NO 243
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 243

Cys Phe Ser Val Glu Ala Gln Thr Cys
    1               5

<210> SEQ ID NO 244
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 244

Cys Phe Ser Val Glu Ala Gln Thr Gly Cys
    1               5                   10

<210> SEQ ID NO 245
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 245

Cys Tyr Phe Ser Val Glu Ala Gln Cys
    1               5

<210> SEQ ID NO 246
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

```
<400> SEQUENCE: 246

Cys Tyr Phe Ser Val Glu Ala Gln Thr Cys
       1               5                  10

<210> SEQ ID NO 247
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 247

Cys Tyr Phe Ser Val Glu Ala Gln Thr Gly Cys
       1               5                  10

<210> SEQ ID NO 248
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 248

Lys Glu Ala Gln Asp
       1               5

<210> SEQ ID NO 249
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 249

Lys Val Glu Ala Gln Asp
       1               5

<210> SEQ ID NO 250
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 250

Lys Glu Ala Gln Thr Asp
       1               5

<210> SEQ ID NO 251
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 251

Lys Ser Val Glu Ala Gln Asp
       1               5

<210> SEQ ID NO 252
<211> LENGTH: 7
```

```
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 252

Lys Val Glu Ala Gln Thr Asp
       1               5

<210> SEQ ID NO 253
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 253

Lys Ser Val Glu Ala Gln Thr Asp
       1               5

<210> SEQ ID NO 254
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 254

Lys Glu Ala Gln Thr Gly Asp
       1               5

<210> SEQ ID NO 255
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 255

Lys Val Glu Ala Gln Thr Gly Asp
       1               5

<210> SEQ ID NO 256
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 256

Lys Ser Val Glu Ala Gln Thr Gly Asp
       1               5

<210> SEQ ID NO 257
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 257

Lys Phe Ser Val Glu Ala Gln Asp
```

```
            1               5
```

<210> SEQ ID NO 258
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 258

```
      Lys Phe Ser Val Glu Ala Gln Thr Asp
        1               5
```

<210> SEQ ID NO 259
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 259

```
      Lys Phe Ser Val Glu Ala Gln Thr Gly Asp
        1               5                  10
```

<210> SEQ ID NO 260
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 260

```
      Lys Tyr Phe Ser Val Glu Ala Gln Asp
        1               5
```

<210> SEQ ID NO 261
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 261

```
      Lys Tyr Phe Ser Val Glu Ala Gln Thr Asp
        1               5                  10
```

<210> SEQ ID NO 262
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 262

```
      Lys Tyr Phe Ser Val Glu Ala Gln Thr Gly Asp
        1               5                  10
```

<210> SEQ ID NO 263
<211> LENGTH: 5
<212> TYPE: PRT
<213> ORGANISM: Artificial Sequence
<220> FEATURE:
<223> OTHER INFORMATION: Synthesized cyclic peptide with an OB-cadherin cell adhesion recognition sequence

<400> SEQUENCE: 263

Glu Glu Ala Gln Lys
     1         5

<210> SEQ ID NO 264
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
     cell adhesion recognition sequence

<400> SEQUENCE: 264

Glu Val Glu Ala Gln Lys
     1         5

<210> SEQ ID NO 265
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
     cell adhesion recognition sequence

<400> SEQUENCE: 265

Glu Glu Ala Gln Thr Lys
     1         5

<210> SEQ ID NO 266
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
     cell adhesion recognition sequence

<400> SEQUENCE: 266

Glu Ser Val Glu Ala Gln Lys
     1         5

<210> SEQ ID NO 267
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
     cell adhesion recognition sequence

<400> SEQUENCE: 267

Glu Val Glu Ala Gln Thr Lys
     1         5

<210> SEQ ID NO 268
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
     cell adhesion recognition sequence

<400> SEQUENCE: 268

Glu Ser Val Glu Ala Gln Thr Lys
     1         5

<210> SEQ ID NO 269

```
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 269

Glu Glu Ala Gln Thr Gly Lys
        1               5

<210> SEQ ID NO 270
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 270

Glu Val Glu Ala Gln Thr Gly Lys
        1               5

<210> SEQ ID NO 271
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 271

Glu Ser Val Glu Ala Gln Thr Gly Lys
        1               5

<210> SEQ ID NO 272
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 272

Glu Phe Ser Val Glu Ala Gln Lys
        1               5

<210> SEQ ID NO 273
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 273

Glu Phe Ser Val Glu Ala Gln Thr Lys
        1               5

<210> SEQ ID NO 274
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 274
```

```
        Glu Phe Ser Val Glu Ala Gln Thr Gly Lys
        1               5                   10

<210> SEQ ID NO 275
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 275

Glu Tyr Phe Ser Val Glu Ala Gln Lys
        1               5

<210> SEQ ID NO 276
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 276

Glu Tyr Phe Ser Val Glu Ala Gln Thr Lys
        1               5                   10

<210> SEQ ID NO 277
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 277

Glu Tyr Phe Ser Val Glu Ala Gln Thr Gly Lys
        1               5                   10

<210> SEQ ID NO 278
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 278

Asp Glu Ala Gln Lys
        1               5

<210> SEQ ID NO 279
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 279

Asp Val Glu Ala Gln Lys
        1               5

<210> SEQ ID NO 280
<211> LENGTH: 6
<212> TYPE: PRT
<213> ORGANISM: Artificial Sequence
<220> FEATURE:
```

<223> OTHER INFORMATION: Synthesized cyclic peptide with an OB-cadherin
      cell adhesion recognition sequence

<400> SEQUENCE: 280

Asp Glu Ala Gln Thr Lys
    1               5

<210> SEQ ID NO 281
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 281

Asp Ser Val Glu Ala Gln Lys
    1               5

<210> SEQ ID NO 282
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 282

Asp Val Glu Ala Gln Thr Lys
    1               5

<210> SEQ ID NO 283
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 283

Asp Ser Val Glu Ala Gln Thr Lys
    1               5

<210> SEQ ID NO 284
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 284

Asp Glu Ala Gln Thr Gly Lys
    1               5

<210> SEQ ID NO 285
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 285

Asp Val Glu Ala Gln Thr Gly Lys
    1               5

```
<210> SEQ ID NO 286
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 286

Asp Ser Val Glu Ala Gln Thr Gly Lys
      1               5

<210> SEQ ID NO 287
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 287

Asp Phe Ser Val Glu Ala Gln Lys
      1               5

<210> SEQ ID NO 288
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 288

Asp Phe Ser Val Glu Ala Gln Thr Lys
      1               5

<210> SEQ ID NO 289
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 289

Asp Phe Ser Val Glu Ala Gln Thr Gly Lys
      1               5                   10

<210> SEQ ID NO 290
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 290

Asp Tyr Phe Ser Val Glu Ala Gln Lys
      1               5

<210> SEQ ID NO 291
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 291
```

```
        Asp Tyr Phe Ser Val Glu Ala Gln Thr Lys
          1               5                  10
```

<210> SEQ ID NO 292
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 292

```
        Asp Tyr Phe Ser Val Glu Ala Gln Thr Gly Lys
          1               5                  10
```

<210> SEQ ID NO 293
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 293

```
        Lys Glu Ala Gln Glu
          1               5
```

<210> SEQ ID NO 294
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 294

```
        Lys Val Glu Ala Gln Glu
          1               5
```

<210> SEQ ID NO 295
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 295

```
        Lys Glu Ala Gln Thr Glu
          1               5
```

<210> SEQ ID NO 296
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 296

```
        Lys Ser Val Glu Ala Gln Glu
          1               5
```

<210> SEQ ID NO 297
<211> LENGTH: 7
<212> TYPE: PRT
<213> ORGANISM: Artificial Sequence

```
<220> FEATURE:
<223> OTHER INFORMATION: Synthesized cyclic peptide with an OB-cadherin
      cell adhesion recognition sequence

<400> SEQUENCE: 297

Lys Val Glu Ala Gln Thr Glu
        1               5

<210> SEQ ID NO 298
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 298

Lys Ser Val Glu Ala Gln Thr Glu
        1               5

<210> SEQ ID NO 299
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 299

Lys Glu Ala Gln Thr Gly Glu
        1               5

<210> SEQ ID NO 300
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 300

Lys Val Glu Ala Gln Thr Gly Glu
        1               5

<210> SEQ ID NO 301
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 301

Lys Ser Val Glu Ala Gln Thr Gly Glu
        1               5

<210> SEQ ID NO 302
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 302

Lys Phe Ser Val Glu Ala Gln Glu
        1               5
```

```
<210> SEQ ID NO 303
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 303

Lys Phe Ser Val Glu Ala Gln Thr Glu
        1               5

<210> SEQ ID NO 304
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 304

Lys Phe Ser Val Glu Ala Gln Thr Gly Glu
        1               5                  10

<210> SEQ ID NO 305
<211> LENGTH: 9
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 305

Lys Tyr Phe Ser Val Glu Ala Gln Glu
        1               5

<210> SEQ ID NO 306
<211> LENGTH: 10
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 306

Lys Tyr Phe Ser Val Glu Ala Gln Thr Glu
        1               5                  10

<210> SEQ ID NO 307
<211> LENGTH: 11
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 307

Lys Tyr Phe Ser Val Glu Ala Gln Thr Gly Glu
        1               5                  10

<210> SEQ ID NO 308
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence
```

```
<400> SEQUENCE: 308

Ser Val Glu Ala Gln
      1               5

<210> SEQ ID NO 309
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 309

Val Glu Ala Gln Thr
      1               5

<210> SEQ ID NO 310
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 310

Ser Val Glu Ala Gln Thr
      1               5

<210> SEQ ID NO 311
<211> LENGTH: 5
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 311

Glu Ala Gln Thr Gly
      1               5

<210> SEQ ID NO 312
<211> LENGTH: 6
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 312

Val Glu Ala Gln Thr Gly
      1               5

<210> SEQ ID NO 313
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 313

Ser Val Glu Ala Gln Thr Gly
      1               5

<210> SEQ ID NO 314
<211> LENGTH: 6
<212> TYPE: PRT
```

```
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 314

Phe Ser Val Glu Ala Gln
        1               5

<210> SEQ ID NO 315
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 315

Phe Ser Val Glu Ala Gln Thr
        1               5

<210> SEQ ID NO 316
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 316

Phe Ser Val Glu Ala Gln Thr Gly
        1               5

<210> SEQ ID NO 317
<211> LENGTH: 7
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 317

Tyr Phe Ser Val Glu Ala Gln
        1               5

<210> SEQ ID NO 318
<211> LENGTH: 8
<212> TYPE: PRT
<213> ORGANISM: Artificial Sequence
<220> FEATURE:
<223> OTHER INFORMATION: Synthesized cyclic peptide with an OB-cadherin
      cell adhesion recognition sequence

<400> SEQUENCE: 318

Tyr Phe Ser Val Glu Ala Gln Thr
        1               5

<210> SEQ ID NO 319
<211> LENGTH: 9
<212> TYPE: PRT
<213> ORGANISM: Artificial Sequence
<220> FEATURE:
```

```
<223> OTHER INFORMATION: Synthesized cyclic peptide with an OB-cadherin
      cell adhesion recognition sequence

<400> SEQUENCE: 319

Tyr Phe Ser Val Glu Ala Gln Thr Gly
       1               5
```